(12) United States Patent
Ramachandran et al.

(10) Patent No.: US 9,804,156 B2
(45) Date of Patent: Oct. 31, 2017

(54) BIOMARKERS FOR SYSTEMIC LUPUS ERYTHEMATOSUS

(71) Applicant: LIFE TECHNOLOGIES CORPORATION, Carlsbad, CA (US)

(72) Inventors: Niroshan Ramachandran, San Marcos, CA (US); Lihao Meng, San Marcos, CA (US); Gengxin Chen, San Mateo, CA (US); David Bourdon, Carlsbad, CA (US); Suzy Van Le, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 13/787,635

(22) Filed: Mar. 6, 2013

(65) Prior Publication Data

US 2014/0011895 A1 Jan. 9, 2014

Related U.S. Application Data

(60) Provisional application No. 61/607,422, filed on Mar. 6, 2012.

(51) Int. Cl.
| | | |
|---|---|---|
| *A61K 38/00* | (2006.01) | |
| *G01N 33/564* | (2006.01) | |
| *G01N 33/68* | (2006.01) | |

(52) U.S. Cl.
CPC ....... *G01N 33/564* (2013.01); *G01N 33/6893* (2013.01); *G01N 2333/52* (2013.01); *G01N 2333/523* (2013.01); *G01N 2800/104* (2013.01); *G01N 2800/52* (2013.01)

(58) Field of Classification Search
CPC .................................................. G01N 33/564
See application file for complete search history.

(56) References Cited

U.S. PATENT DOCUMENTS

| | | | |
|---|---|---|---|
| 6,268,222 B1 | 7/2001 | Chandler et al. | |
| 6,306,610 B1 | 10/2001 | Bawendi et al. | |
| 6,342,221 B1 | 1/2002 | Thorpe et al. | |
| 6,592,822 B1 | 7/2003 | Chandler | |
| 6,599,331 B2 | 7/2003 | Chandler et al. | |
| 2006/0094056 A1* | 5/2006 | Chappell | G01N 33/564 435/7.1 |

OTHER PUBLICATIONS

Lu et al., (Rheumatol Int. May 2012;32(5):1231-3).*
Vila et al., (Clin Rheumatol. May 2007;26(5):718-22. Epub Aug. 19, 2006).*
Hu et al., (Proteomics. Apr. 2011;11(8):1499-507. Epub Mar. 17, 2011).*
Luft et al., (J Rheumatol. Dec. 2003;30(12):2613-9).*
Tanay et al., (IMAJ. Nov. 2002;4:11. Suppl Nov. 2002, pp. 878-879).*

(Continued)

*Primary Examiner* — Cherie M Stanfield
(74) *Attorney, Agent, or Firm* — Porter Wright Morris & Arthur LLP

(57) ABSTRACT

The disclosure provides SLE biomarkers. The disclosure further provides kits and methods of diagnosing, prognosing, and stratifying subjects with the disease by utilizing SLE biomarkers.

19 Claims, 9 Drawing Sheets

(56) References Cited

OTHER PUBLICATIONS

Bolton, A E. et al., "Radioimmunoassay and Related Materials", *Handbook of Experimental Immunology*, Weir, D.M. ed., Blackwell Scientific Publications (textbook), 1996.

Fahrlander, Paul D. et al., "Amplifying DNA Probe Signals: A 'christmas Tree' Approach", *Bio/Technology*, vol. 6, 1988, 1165-1168.

Hanley, et al., "The Meaning and use of the Area Under a Receiver Operating Characteristic (ROC) Curve", *Radiology*, 143, 1982, 29-36.

Kohler, G. et al., "Continuous cultures of fused cells secreting antibody of predefined specificity", *Nature*, vol. 256, Aug. 7, 1975, 495-497.

Korsgren, Catherine et al., "Complete amino acid sequence and homologies of human erythrocyte membrane protein band 4.2", *Proc. Natl. Acad. Sci.*, vol. 87, 1990, 613-617.

Ross, Jeffrey S. et al., "Targeted Therapy in Breast Cancer: The HER-2/neu Gene and Protein", *Molecular & Cellular Proteomics*, vol. 3, No. 4, Apr. 2004, 379-398.

Vignali, Dario A. et al., "Multiplexed Particle-Based Flow Cytometric Assays", *Journal of Immunological Methods*, vol. 243, No. 1-2, Sep. 2000, 243-255.

PCT/US2013/029452 International Search Report dated Jun. 28, 2013.

PCT/US2013/029452 International Written Opinion dated Jun. 28, 2013.

Ansari, N et al., "Comparison of RANTES expression in Crohn's disease and ulcerative colitis: an aid in the differential diagnosis", *Journal of Clinical Pathology*, BMJ Publishing Group, GB;, vol. 59(10), XP008146728,_ 2006, 1066-1072.

Feighery, L et al., "Anti-transglumatminase antibodies and the serological diagnosis of coeliac disease", *British Journal of Biomedical Science, Royal Society of Medicine Services, Longon, GB*; vol. 60(1), XP008162835; 2003, 14-18.

Hu, S. et al., "Identification of autoantibody biomarkers for primary Sjögren's syndrome using protein microarrays", *Proteomics*, vol. 11( 8), XP055065747, 2011, 1499-1507.

Lu, M. et al., "Increased serum RANTES in patients with systemic lupus erythematosus", *Rheumatology International*, vol. 32( 5) ,_XP55065449, 2011, 1231-1233.

Luft, L. et al., "Autoantibodies to Tissue Transglutaminase in Sjögren's Syndrome and Related Rheumatic Diseases", *The Journal of Rheumatology*, vol. 30(12), 2003, 2613-2619.

Szodoray, P et al., "Circulating Cytokines in Primary Sjögren's Syndrome Determined by a Multiplex Cytokine Array System", *Scandinavian Journal of Immunology, Blackwell Science Publ., Oxford, GB*; vol. 59( 6), XP001203983,_ 2004, 592-599.

Tanay, A. et al., "TG or not TG: IgG-Anti-Tissue Transglutaminase in Systemic Lupus Erythematosus: New Role for an Old Enzyme", *Clinical Immunology and Allergy, Suppl*, vol. 4(11) , XP008162849, 2002, 878-879.

Torok, H. et al., "Increased serum levels of anti-tissue transglutaminase antibodies in patients with ulcerative colitis", *Gastroenterology* (online) vol. 130(4), Suppl. 2; XP008162840, 2006, A361.

Vila, L.. et al., "Association of serum of MIP-1[alpha], MIP-1[beta], and RANTES with clinical manifestations, disease activity, and damage accrual in systemic lupus erythematosus", *Clinical Rheumatology; Journal of the International League of Associations for Rheumatology, Springer-Verlag, Lo*, vol. 26(5), XP019494526;_2006, 718-722.

\* cited by examiner

| Gene symbol | Accession ID | Ultimate ORF ID | Prevalence in SLE | Prevalence in controls + other diseases | Statistical significance (p value) |
|---|---|---|---|---|---|
| DDX54 | BC001132.1 | IOH3853 | 0.383562 | 0.099099 | 3.90E-06 |
| C1orf77 | BC002733.2 | IOH5365 | 0.39726 | 0.09009 | 1.61E-06 |
| NPM1 | BC021983.1 | IOH27884 | 0.356164 | 0.108108 | 4.85E-05 |
| EIF2C1 | BC063275.1 | IOH40423 | 0.465753 | 0.081081 | 1.35E-08 |
| HMGN1 | BC070154.1 | IOH63011 | 0.424658 | 0.072072 | 8.27E-09 |
| RPS19 | NM_001022.3 | IOH4572 | 0.356164 | 0.072072 | 1.13E-06 |
| RDBP | NM_002904.4 | IOH14621 | 0.315068 | 0.027027 | 1.76E-08 |
| SNRP70 | NM_003089.4 | IOH40192 | 0.452055 | 0.108108 | 1.05E-07 |
| METTL1 | NM_005371.2 | IOH4172 | 0.356164 | 0.081081 | 3.27E-06 |
| PIN4 | NM_006223.1 | IOH7192 | 0.383562 | 0.099099 | 2.18E-05 |
| EIF2C4 | NM_017629.2 | IOH38411 | 0.328767 | 0.054054 | 6.79E-07 |
| C3orf26 | NM_032359.1 | IOH5762 | 0.342466 | 0.072072 | 2.81E-06 |
| MRPS6 | NM_032476.1 | IOH13845 | 0.369863 | 0.081081 | 1.33E-06 |
| PPP1R14A | NM_033256.1 | IOH13214 | 0.493151 | 0.126126 | 1.06E-07 |
| C1orf83 | NM_153035.1 | IOH27410 | 0.356164 | 0.081081 | 3.27E-06 |

FIG. 3

Cytokines

| Diagnosed | Panel-classified | |
|---|---|---|
| | SLE | Non SLE |
| SLE | 91 | 1 |
| Non SLE | 2 | 83 |

98% predictive

IL 13, IL 12, RANTES, Eotaxin, IL 2R

FIG. 8A

Antibodies

| Diagnosed | Panel-classified | |
|---|---|---|
| | SLE | Non SLE |
| SLE | 65 | 27 |
| Non SLE | 8 | 77 |

80% predictive cardiolipin, CENP B, Jo-1, Mi-2b myeloperoxidase Ro/SS-A, Smith antigen, thyroglobulin, thyroid peroxidase

FIG. 8B

Cytokines & antibodies

| Diagnosed | Panel-classified | |
|---|---|---|
| | SLE | Non SLE |
| SLE | 91 | 1 |
| Non SLE | 2 | 83 |

98% predictive

RANTES & transglutaminase

FIG. 8C

SEQUENCE LISTING

```
<160> NUMBER OF SEQ ID NOS: 4

<210> SEQ ID NO 1
<211> LENGTH: 91
<212> TYPE: PRT
<213> ORGANISM: Homo sapiens

<400> SEQUENCE: 1

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 2
<211> LENGTH: 224
<212> TYPE: PRT
<213> ORGANISM: Homo sapiens

<400> SEQUENCE: 2

Arg Arg Gly Ser Val Pro Ile Leu Arg Gln Trp Leu Thr Gly Arg Gly
1               5                   10                  15

Arg Pro Val Tyr Asp Gly Gln Ala Trp Val Leu Ala Ala Val Ala Cys
                20                  25                  30

Thr Val Leu Arg Cys Leu Gly Ile Pro Ala Arg Val Val Thr Thr Phe
            35                  40                  45

Ala Ser Ala Gln Gly Thr Gly Gly Arg Leu Leu Ile Asp Glu Tyr Tyr
        50                  55                  60

Asn Glu Glu Gly Leu Gln Asn Gly Glu Gly Gln Arg Gly Arg Ile Trp
65                  70                  75                  80

Ile Phe Gln Thr Ser Thr Glu Cys Trp Met Thr Arg Pro Ala Leu Pro
                85                  90                  95

Gln Gly Tyr Asp Gly Trp Gln Ile Leu Asp Pro Ser Ala Pro Asn Gly
                100                 105                 110

Gly Gly Val Leu Gly Ser Cys Asp Leu Val Pro Val Arg Ala Val Lys
```

```
                115                    120                    125
Glu Gly Thr Val Gly Leu Thr Pro Ala Val Ser Asp Leu Phe Ala Ala
            130                    135                    140

Ile Asn Ala Ser Cys Val Val Trp Lys Cys Cys Glu Asp Gly Thr Leu
145                 150                    155                    160

Glu Leu Thr Asp Ser Asn Thr Lys Tyr Val Gly Asn Asn Ile Ser Thr
                165                    170                    175

Lys Gly Val Gly Ser Asp Arg Cys Glu Asp Ile Thr Gln Asn Tyr Lys
            180                    185                    190

Tyr Pro Glu Gly Ser Leu Gln Glu Lys Glu Val Leu Glu Arg Val Glu
                195                    200                    205

Lys Glu Lys Met Glu Arg Glu Lys Asp Asn Gly Ile Arg Pro Pro Ser
            210                    215                    220

<210> SEQ ID NO 3
<211> LENGTH: 227
<212> TYPE: PRT
<213> ORGANISM: Cavia sp.

<400> SEQUENCE: 3

Ser Pro Met Ser Trp Ile Gly Ser Val Asp Ile Leu Arg Arg Trp Lys
1               5                   10                  15

Asp Tyr Gly Cys Gln Arg Val Lys Tyr Gly Gln Cys Trp Val Phe Ala
            20                  25                  30

Ala Val Ala Cys Thr Val Leu Arg Cys Leu Ala Ile Pro Thr Arg Val
        35                  40                  45

Val Thr Asn Phe Asn Ser Ala His Asp Gln Asn Ser Asn Leu Leu Ile
    50                  55                  60

Glu Tyr Phe Arg Asn Glu Ser Gly Glu Ile Glu Gly Asn Lys Ser Glu
65                  70                  75                  80

Met Ile Trp Asn Phe His Ser Leu Leu Gly Gly Val Val Asp Asp Gln
                85                  90                  95

Ala Gly Pro Gly Ala Trp Val Arg Gly Val Gln Ala Leu Asp Pro Thr
            100                 105                 110

Pro Gln Glu Lys Ser Gly Gly Thr Tyr Cys Cys Gly Pro Val Pro Val
        115                 120                 125

Arg Ala Ile Lys Glu Gly His Leu Asn Val Lys Tyr Asp Ala Pro Phe
    130                 135                 140

Val Phe Ala Glu Val Asn Ala Asp Val Val Asn Trp Ile Arg Gln Lys
145                 150                 155                 160

Asp Gly Ser Leu Arg Lys Ser Ile Asn His Leu Val Val Gly Leu Lys
                165                 170                 175

Ile Ser Thr Lys Ser Val Gly Arg Asp Glu Arg Glu Asp Ile Thr His
            180                 185                 190

Thr Tyr Lys Tyr Pro Glu Gly Ser Glu Glu Arg Glu Ala Phe Val
        195                 200                 205

Arg Ala Asn His Leu Asn Lys Leu Ala Thr Lys Glu Glu Ala Gln Glu
    210                 215                 220

Glu Thr Gly
225

<210> SEQ ID NO 4
<211> LENGTH: 217
<212> TYPE: PRT
<213> ORGANISM: Homo sapiens
```

-continued

```
<400> SEQUENCE: 4

Gly Ser Val Asp Ile Leu Leu Glu Tyr Arg Ser Ser Glu Asn Pro Val
1               5                   10                  15

Arg Tyr Gly Gln Cys Trp Val Phe Ala Gly Val Phe Asn Thr Phe Leu
                20                  25                  30

Arg Cys Leu Gly Ile Pro Ala Arg Ile Val Thr Asn Tyr Phe Ser Ala
            35                  40                  45

His Asp Asn Asp Ala Asn Leu Gln Met Asp Ile Phe Leu Glu Glu Asp
        50                  55                  60

Gly Asn Val Asn Ser Lys Leu Thr Lys Asp Ser Val Trp Asn Tyr His
65                  70                  75                  80

Cys Trp Asn Glu Ala Trp Met Thr Arg Pro Asp Leu Pro Val Gly Phe
                85                  90                  95

Gly Gly Trp Gln Ala Val Asp Ser Thr Pro Gln Glu Asn Ser Asp Gly
            100                 105                 110

Met Tyr Arg Cys Gly Pro Ala Ser Val Gln Ala Ile Lys His Gly His
            115                 120                 125

Val Cys Phe Gln Phe Asp Ala Pro Phe Val Phe Ala Glu Val Asn Ser
        130                 135                 140

Asp Leu Ile Tyr Ile Thr Ala Lys Lys Asp Gly Thr His Val Val Glu
145                 150                 155                 160

Asn Val Asp Ala Thr His Ile Gly Lys Leu Ile Val Thr Lys Gln Ile
                165                 170                 175

Gly Gly Asp Gly Met Met Asp Ile Thr Asp Thr Tyr Lys Phe Gln Glu
            180                 185                 190

Gly Gln Glu Glu Glu Arg Leu Ala Leu Glu Thr Ala Leu Met Tyr Gly
        195                 200                 205

Ala Lys Lys Pro Leu Asn Thr Glu Gly
210                 215
```

BIOMARKERS FOR SYSTEMIC LUPUS ERYTHEMATOSUS

RELATED APPLICATIONS

This application claims the benefit of the filing date of U.S. provisional patent application 61/607,422, filed Mar. 6, 2012 and entitled "BIOMARKERS FOR SYSTEMIC LUPUS ERYTHEMATOSUS," the contents of which are incorporated by reference.

BACKGROUND

Systemic lupus erythematosus (SLE or "lupus") is an autoimmune disorder that can affect multiple organs, including the heart, joints, skin, lungs, blood vessels, liver, kidneys, and nervous system. SLE diagnosis can be difficult because of varying symptoms which have different durations and effects on patients. This difficulty can cause lupus to be a fatal disease if misdiagnosed. SLE predominantly affects women of non-European descent, and is estimated to affect more than 250,000 patients in the United States. While SLE symptoms can be managed by immuno-suppression therapy, there are presently no cures.

While several clinical markers presently exist for SLE, these markers have poor sensitivity and specificity, limiting their effectives. Given the complexity of SLE diagnosis, the broad populations it impacts, and the number of treatments available and in development, effective biomarkers are needed both for diagnosis and to better stratify patient samples so that appropriate treatments can be administered to improve patient survival and quality of life.

Disclosed herein are biomarkers and methods that provide method for detecting and diagnosing SLE.

BRIEF SUMMARY

Currently no single test establishes the diagnosis of SLE. To help doctors improve the accuracy of diagnosis of SLE, eleven criteria were established by the American Rheumatism Association. These eleven criteria are closely related to the variety of symptoms observed in patients with SLE. When a person has four or more of these criteria, the diagnosis of SLE is strongly suggested. However, some patients suspected of having SLE may never develop enough criteria for a definite diagnosis. Other patients accumulate enough criteria only after months or years of observation. Nevertheless, the diagnosis of SLE may be made in some settings in patients with only a few of these classical criteria. Of these patients, a number may later develop other criteria, but many never do.

The eleven criteria conventionally used for diagnosing SLE include: malar over the cheeks of the face or "butterfly" rash; discoid skin rash; photosensitivity; mucus membrane ulcers; arthritis; pleuritis/pericarditis; kidney abnormalities; seizures (convulsions) and/or psychosis; blood count abnormalities; immunologic disorder; and positive for antinuclear antibodies.

Although these criteria serve as useful reminders of those features that distinguish lupus from other related autoimmune diseases, they are unavoidably fallible.

Accordingly, in some embodiments is provided a kit for diagnosing SLE comprising: a) a target antigen comprising an antigen of Table II or III or a fragment thereof comprising an epitope; and b) means for detecting binding of one or more molecules in a test sample to the target antigen.

In another embodiment, the disclosure provides a method of diagnosing systemic lupus erythematosus (SLE) in an individual suspected of having SLE comprising: a) contacting a test sample with one or more affinity reagents that specifically bind a cytokine b) contacting the test sample with an affinity reagent that specifically binds a human antibody, wherein the human antibody binds any one of the polypeptides found in Table II or Table III, or a fragment thereof comprising an epitope recognized by a human antibody, b) detecting binding of one or more of the affinity reagents using an immunoassay; c) detecting the binding in a sample from a control individual without SLE using an immunoassay and d) comparing the detectable binding found in the test sample to that of a control individual without SLE, wherein a detectable signal greater in the test sample relative to the control is indicative of SLE. In some embodiments, the immunoassay is a protoplex immune response assay.

In another embodiment, a mixture is disclosed comprising: a) one or more target antigens of Table II or III or a fragment thereof comprising an epitope; b) more than one affinity reagent and c) a test sample from an individual suspected of having SLE.

Further embodiments provide methods of prognosing and stratifying subjects with SLE utilizing the cytokines and antigens of Tables II and III.

DESCRIPTION OF THE DRAWINGS

FIG. 3 is a table of 15 novel SLE antigens characterized for corresponding immune response using PROTOPLEX™ Immune Response Assay. Prevalence of response with SLE samples and controls were calculated. Significance was calculated using M statistics.

FIG. 8A-C is a series of matching matrices (also referred to as "confusion matrices"). These matrices highlight SLE predictive panels (A) cytokines; (B) antibodies to particular identified proteins; and (C) the combination of cytokines and antibodies to particular identified proteins). Sera of known diagnosis origin were analyzed for cytokine concentrations or antibody levels to specified antigens. True positive (upper left) and true negative (lower right) correspond to the noted predictive value of each panel.

DETAILED DESCRIPTION

Figure 1:
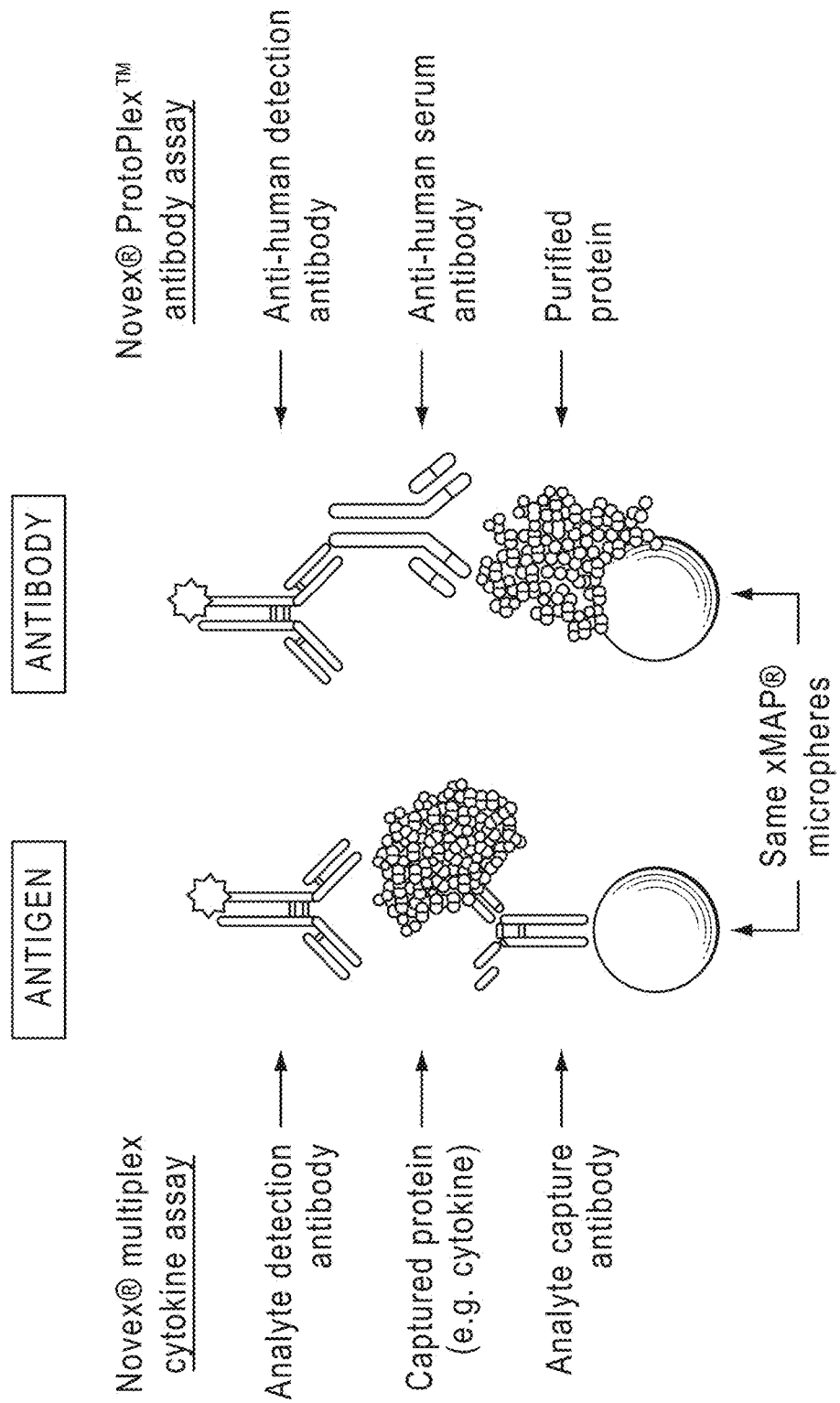
FIG. 1 is a schematic of the PROTOPLEX™ Immune Response Assay design with respect to the well-established Novex antigen detection immunoassay.

The present disclosure provides biomarkers and a biomarker panel(s) highly indicative for systemic lupus erythematosus (SLE) and thereby permitting a more accurate assessment of whether an individual is suffering from SLE. Furthermore, the disclosed biomarker panel(s) can distinguish between an individual with SLE and another disease. For example, using the biomarker panel(s) disclosed herein, it is possible to distinguish between SLE and other diseases such as Crohn's disease, rheumatoid arthritis and multiple sclerosis. Therefore, the disclosed biomarker panel(s) may be used in the diagnosis of SLE.

SLE is a systemic autoimmune disease characterized by the production of autoantibodies directed against nuclear self-antigens and circulating immune complexes. This results in damage to various organs or systems, including skin, joints, kidneys and the central nervous system. Clinical manifestations of SLE can be diverse, and can include glomerulonephritis, dermatitis, thrombosis, vasculitis, seizures and arthritis. Because of this heterogeneity, the accurate and early identification of SLE is challenging.

Accordingly, the instant disclosure provides, in part, kits, and methods of their use, combining affinity reagents for the capture and/or detection of one or more cytokines and one or more antibodies that recognize particular antigens in a biological sample. The combination of the detection of cytokine(s) and antibody(ies) that recognize particular antigens being highly correlative with SLE.

By "affinity reagent," "binding ligand," "capture binding ligand," "capture binding species," "capture probe" or "capture ligand" herein is meant a compound that is used to detect the presence of or to quantify, relatively or absolutely, a target analyte or target species and that will bind to the target analyte or target species. Binding ligands include proteins, particularly including antibodies or fragments thereof as discussed further below.

Generally, the capture binding ligand allows the attachment of a target species or target sequence to a solid support for the purposes of detection as further described herein. Attachment of the target species to the capture binding ligand may be direct or indirect.

In some embodiments, the instant disclosure provides kits, and methods of their use, combining a first and a second affinity reagent for the capture and/or detection of a cytokine and an affinity reagent for the capture and/or detection of an antibody that specifically binds a polypeptide, or a fragment of, disclosed in Table II or Table III.

A "cytokine" is any secreted polypeptide that affects the functions of other cells, and is a molecule that modulates interactions between cells in the immune or inflammatory response. Cytokines include, but are not limited to, monokines, chemokines and lymphokines regardless of the cells that produce them. For instance a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and B-lymphocytes. Lymphokines are generally referred to as being produced by lymphocyte cells.

Examples of cytokines include, but are not limited to, Regulated and Normal T Cell Expressed and Secreted (RANTES), epidermal growth factor (HGF), interleukin-2 (IL-2), interleukin-15 (IL-15), human growth factor (HGF), interleukin-7 (IL-7), macrophage inflammatory protein-1 alpha (MIP-1α), eotaxin, interleukin-17 (IL-17), interferon-α (IFN-α), interleukin-8 (IL-8), macrophage inflammatory protein-1 beta (MIP-1β). Fibroblast growth factor-basic (bFGF), interleukin-4 (IL-4), interferon gamma-induced protein 10 (IP-10), interferon-gamma (IFN-γ), interleukin-10 (IL-10), granulocyte colony-stimulating factor (G-CSF), interleukin-5 monocyte chemotactic protein-1 (MCP-1), interleukin-12 (IL-12), tumor necrosis factor-alpha (TNF-α), granulocyte-macrophage colony-stimulating factor (GM-CSF), interleukin-6 (IL-6), monokine induced by gamma interferon (MIG), interleukin-1 beta (IL-1β), interleukin-13 (IL-13) and vascular endothelial growth factor (VEGF) and regulated and normal T cell expressed and secreted (RANTES).

In some embodiments, the cytokine specifically bound by one or more affinity reagents is RANTES. RANTES, also referred to as chemokine (C-C motif) ligand 5 (CCL5), is a protein which is humans is encoded by the cc15 gene. Schlecker et al. (2012). The polypeptide sequence of RANTES is provided in SEQ ID NO:1 and appears as GenBank accession NP_002976.2.

(RANTES)

SEQ ID NO: 1

MKVSAAALAVILIATALCAPASASPYSSDTTPCCFAYIARPLPRAHIKEY

FYTSGKCSNPAVVFVTRKNR QVCANPEKKWVREYINSLEMS

In some embodiments, the one or more affinity reagents are an antibody. "Antibody" refers to a polypeptide substantially encoded by an immunoglobulin gene or immunoglobulin genes, or fragments thereof, which specifically binds and recognizes an epitope. The recognized immunoglobulin genes include the kappa and lambda light chain constant region genes, the alpha, gamma, delta, epsilon and mu heavy chain constant region genes, and a myriad of immunoglobulin variable region genes. Antibodies exist, for example, as intact antibodies or as a number of well characterized fragments produced by digestion with various peptidases. This includes, for example, Fab' and F(ab')$_2$ fragments.

Thus, in some embodiments, a kit and a method of its use are provided, encompassing a first and a second antibody, wherein the first and the second antibody specifically bind RANTES and a third antibody that specifically binds an antibody that specifically binds any one of the polypeptides, or fragments thereof, provided in Tables II and III.

The term antibody also includes polyclonal antibodies and monoclonal antibodies. The terms "polyclonal antibody" and "polyclonal antibodies" as used herein refer to a heterogeneous mixture of antibody molecules which is capable of binding to or reacting with several different epitopes on the same antigen. Polyclonal antibody preparations isolated from the blood, milk, colostrum or eggs of immunized animals typically include antibodies that are not specific for the target antigen in addition to antibodies specific for the target antigen. Thus, the term "polyclonal antibody" as used herein refers both to antibody preparations in which the antibody specific for a particular antigen has been enriched, for example, by antigen affinity chromatography, and to preparations that are not so enriched.

Accordingly, in some embodiments, one or more antibodies are a polyclonal antibody or antibodies preparation. In other embodiments, one or more antibodies are monoclonal antibodies. A "monoclonal" antibody refers to an antibody produced by a single hybridoma (or clone thereof) or other cell line, or by a transgenic animal such that the monoclonal antibody will typically recognize one epitope on the antigen. A monoclonal antibody composition displays a single binding specificity for a particular epitope.

The term antibody, also includes antibody fragments either produced by the modification of whole antibodies or those synthesized de novo using recombinant DNA methodologies. Antibodies can be a variety of structures, including, but not limited to, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In some embodiments, an antibody is provided that specifically binds the fragment crystallizable region of an autoantibody. The "Fragment Crystallizable region," "Fc region," "Fc domain," "Fc" portion of an antibody refers to that portion of an immunoglobulin heavy chain that comprises one or more heavy chain constant region domains, $C_H1$, $C_H2$ and $C_H3$, but does not include the heavy chain variable region.

In other embodiments is provided an antibody that specifically binds the constant region of the antibody light chain (kappa and/or lambda).

"Autoantibody" refers to antibody produced by the immune system of a subject that is directed to, and specifically binds to, a naturally occurring epitope in the subject.

In some embodiments, the subject is a human and an antibody that specifically binds an epitope naturally occurring in humans is detected; that is, the detected antibody is an autoantibody and the antigen bound by the autoantibody is an autoantigen. Thus, in some embodiments, a kit and a method of its use are provided, encompassing a first and a second antibody, wherein the first and the second antibody specifically bind RANTES and a third antibody specifically binds a human autoantibody. In some embodiments, the third antibody specifically binds an antibody that specifically binds any one of the polypeptides, or fragments thereof, provided in Tables II and III.

The antibody hypervariable region, also referred to as the complementary determining region (CDR) contributes to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

Epitopes can be either conformational or linear. A conformational epitope is produced by spatially juxtaposed amino acids from different segments of the linear polypeptide chain. A linear epitope is one produced by adjacent amino acid residues in a polypeptide chain.

Conformational and nonconformational epitopes may be distinguished in that the binding to the former but not the latter is lost in the presence of denaturing solvents. An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning."

An "antigen" as used herein refers to molecules such as nucleic acids, lipids, carbohydrates, proteoglycans, ribonucleoprotein complexes, protein complexes, proteins, glycoproteins, polypeptides, peptides, lipids, glycolipids, and naturally occurring or synthetic (in vitro) modifications of such molecules against which an immune response involving B lymphocytes can be generated. For each antigen, there exists more than one epitope.

As used herein, "target antigen" refers to a protein, or to a portion, fragment, variant, isoform, processing product thereof having immunoreactivity of the protein, that is used to determine the presence, absence, or amount of an antibody in a sample from a subject. A "test antigen" is a protein evaluated for use as a target antigen. A test antigen is therefore a candidate target antigen, or a protein used to determine whether a portion of a test population has antibodies reactive against it.

Use of the terms "target antigen" and "test antigen" is meant to include the complete wild type mature protein, or can also denote a precursor, processed form (including, a proteolytically processed or otherwise cleaved form) unprocessed form, post-translationally modified, or chemically modified form of the protein indicated, in which the target antigen, test antigen, or antigen retains or possesses the specific binding characteristics of the referenced protein to one or more antibodies of a test sample. The protein can have, for example, one or more modifications not typically found in the protein produced by normal cells, including aberrant processing, cleavage or degradation, oxidation of amino acid residues, atypical glycosylation pattern, etc. The use of the terms "target antigen" or "test antigen" also include splice isoforms or allelic variants of the referenced proteins, or can be sequence variants of the referenced protein, with the proviso that the "target antigen" and the "test antigen" retain or possess the immunological reactivity of the referenced protein to one or more autoantibodies of a test sample. Use of the term "target antigen" and "test antigen," encompasses fragments of a referenced protein ("antigenic fragments") that have the antibody binding specificity of the reference protein.

As used herein, the word "protein" refers to a full-length protein, a portion of a protein, or a peptide. Proteins can be produced via fragmentation of larger proteins, or chemically synthesized. Proteins may, for example, be prepared by recombinant overexpression in a species such as, but not limited to, bacteria, yeast, insect cells, and mammalian cells. Proteins to be placed in a protein microarray of the invention, may be, for example, are fusion proteins, for example with at least one affinity tag to aid in purification and/or immobilization. In certain aspects of the invention, at least 2 tags are present on the protein, one of which can be used to aid in purification and the other can be used to aid in immobilization. In certain illustrative aspects, the tag is a His tag, a GST tag, or a biotin tag. Where the tag is a biotin tag, the tag can be associated with a protein in vitro or in vivo using commercially available reagents (Invitrogen, Carlsbad, Calif.). In aspects where the tag is associated with the protein in vitro, a Bioease tag can be used (Invitrogen, Carlsbad, Calif.).

As used herein, the term "peptide," "oligopeptide," and "polypeptide" are used interchangeably with protein herein and refer to a sequence of contiguous amino acids linked by peptide bonds. As used herein, the term "protein" refers to a polypeptide that can also include post-translational modifications that include the modification of amino acids of the protein and may include the addition of chemical groups or biomolecules that are not amino acid-based. The terms apply to amino acid polymers in which one or more amino acid residue is an analog or mimetic of a corresponding naturally occurring amino acid, as well as to naturally occurring amino acid polymers. Polypeptides can be modified, for example, by the addition of carbohydrate residues to form glycoproteins. The terms "polypeptide," "peptide" and "protein" include glycoproteins, as well as non-glycoproteins.

A "variant" of a polypeptide or protein, as used herein, refers to an amino acid sequence that is altered with respect to the referenced polypeptide or protein by one or more amino acids. Preferably a variant of a polypeptide has at least 60% identity to the referenced protein over a sequence of at least 15 amino acids. More preferably a variant of a polypeptide is at least 70% identical to the referenced protein over a sequence of at least 15 amino acids. Protein variants can be, for example, at least 80%, at least 90%, at least 95%, or at least 99% identical to referenced polypeptide over a sequence of at least 15 amino acids. Protein variants of the invention can be, for example, at least 80%, at least 90%, at least 95%, or at least 99% identical to referenced polypeptide over a sequence of at least 20 amino acids. The variant may have "conservative" changes, wherein a substituted amino acid has similar structural or chemical properties (for example, replacement of leucine with isoleucine). A variant may also have "nonconservative" changes (for example, replacement of glycine with tryptophan). Analogous minor variations may also include amino acid deletions or insertions, or both.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

The phrase "selectively binds" to an antibody or "selectively immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. For example, solid-phase ELISA immunoassays are routinely used to select antibodies specifically immunoreactive with a protein (see, for example, Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

In some embodiments, a kit and a method of its use are provided, encompassing a first and a second antibody, wherein the first and the second antibody specifically bind RANTES, a third antibody that specifically binds a human antibody that specifically binds anyone of the proteins, or fragments thereof provided in Tables II and III, and a purified antigen. In other embodiments, the human antibody is an autoantibody.

In other embodiments, a kit and a method of its use are provided, wherein the first and second antibodies that bind RANTES are monoclonal antibodies and wherein the first and second antibodies recognize distinct epitopes.

The terms "purified" and "isolated" as used herein, are synonymous, and refer to a material that is substantially or essentially free from other components. For example, in one embodiment, a recombinant protein is isolated or purified when it is free from other components used in the cloning reaction, or solid state synthesis, isolation or purity is generally determined using analytical chemistry techniques such as polyacrylamide gel electrophoresis, mass spectrometry, or high performance liquid chromatography (HPLC). In one embodiment, a polynucleotide, protein or peptide of the present invention is considered to be isolated when it is the predominant species present in a preparation. A purified protein, peptide or nucleic acid molecule of the invention represents greater than about 80% of the macromolecular species present, greater than about 90% of the macromolecular species present, greater than about 95% of the macromolecular species present, greater than about 96% of the macromolecular species present, greater than about 97% of the macromolecular species present, greater than about 98% of the macromolecular species present, greater than about 99% of the macromolecular species present in a preparation.

In some embodiments, a purified antigen is provided, wherein the purified antigen is transglutaminase. "Transglutaminase" refers to an enzyme family that catalyzes the formation of a covalent bond between a free amine group and the gamma-carboxamide group of protein or peptide bound glutamine. Members of the transglutaminase family include Factor XIII, keratinocyte transglutaminase, tissue transglutaminase, epidermal transglutaminase, prostate transglutaminase, TGM X, TGM Y, TGM Z and erythrocyte band 4.2. Korsgren et al. describe the amino acid sequences of erythrocyte band 4.2, guinea pig liver transglutaminase and the a subunit of human factor XIII and the nucleic acid sequence for erythrocyte band 4.2. Proc. Nat'l Acad. Sci. USA (1990) 87:613-617. The amino acid sequence of each of these is as follows:

(erythrocyte band 4.2)
SEQ ID NO: 2
RRGSVPILRQWLTGRGRPVYDGQAWVLAAVACTVLRCLGIPARVVTTFAS

AQGTGGRLLIDEYYNEEGLQNGEGQRGRIWIFQTSTECWMTRPALPQGYD

GWQILDPSAPNGGGVLGSCDLVPVRAVKEGTVGLTPAVSDLFAAINASCV

VWKCCEDGTLELTDSNTKYVGNNISTKGVGSDRCEDITQNYKYPEGSLQE

KEVLERVEKEKMEREKDNGIRPPS

-continued (guinea pig liver transglutaminase)
SEQ ID NO: 3
SPMSWIGSVDILRRWKDYGCQRVKYGQCWVFAAVACTVLRCLAIPTRVVT

NFNSAHDQNSNLLIEYFRNESGEIEGNKSEMIWNFHSLLGGVVDDQAGPG

AWVRGVQALDPTPQEKSEGTYCCGPVPVRAIKEGHLNVKYDAPFVFAEVN

ADVVNWIRQKDGSLRKSINHLVVGLKISTKSVGRDEREDITHTYKYPEGS

EEEREAFVRANHLNKLATKEEAQEETG (a subunit Factor XIII)
SEQ ID NO: 4
GSVDILLEYRSSENPVRYGQCWVFAGVFNTFLRCLGIPARIVTNYFSAHD

NDANLQMDIFLEEDGNVNSKLTKDSVWNYHCWNEAWMTRPDLPVGFGGWQ

AVDSTPQENSDGMYRCGPASVQAIKHGHVCFQFDAPFVFAEVNSDLIYIT

AKKDGTHVVENVDATHIGKLIVTKQIGGDGMMDITDTYKFQEGQEEERLA

LETALMYGAKKPLNTEG

In some embodiments, a kit and a method of its use are provided, encompassing a first and a second antibody, wherein the first and the second antibody specifically bind RANTES, a third antibody that specifically binds a human antibody that specifically binds a transglutaminase. In some embodiments, the human antibody specifically binds guinea pig liver transglutaminase. In other embodiments, the human antibody specifically binds a guinea pig liver transglutaminase epitope.

Arrays

The present disclosure is based, in part, on the identification of antibodies with reactivities associated with SLE. Serum samples from healthy individuals as well as patients with autoimmune diseases, were profiled on PROTOARRAY™ human protein microarrays (Invitrogen Corporation, Carlsbad, Calif.), described in more detail below, to identify multiple SLE-specific biomarkers. The extensive content of the arrays, including lower abundance proteins, native conformation, and insect cell-derived post-translational modifications, enabled the identification of biomarkers not previously known to be associated with SLE.

Microarrays, or other assay formats, containing these biomarkers are able to detect the presence of antibodies in a patient sample that bind the biomarkers, enabling the diagnosis and monitoring of the disease. Microarrays or other assays can contain specific biomarkers or a specific group of biomarkers, such as those associated with SLE.

As used herein, the term "array" refers to an arrangement of entities in a pattern on a substrate. Although the pattern is typically a two-dimensional pattern, the pattern may also be a three-dimensional pattern. In a protein array, the entities are proteins. In certain embodiments, the array can be a microarray or a nanoarray. A "nanoarray" is an array in which separate entities are separated by 0.1 nm to 10 μm, for example from 1 nm to 1 μm. A "microarray" is an array in the density of entities on the array is at least 100/cm². On microarrays separate entities can be separated, for example, by more than 1 μm.

The term "protein array" as used herein refers to a protein array, a protein microarray or a protein nanoarray. A protein array may include, for example, but is not limited to, a "PROTOARRAY™," protein high density array (Invitrogen, Carlsbad, Calif., available on the Internet at Invitrogen.com). The PROTOARRAY™ high density protein array can be used to screen complex biological mixtures, such as serum, to assay for the presence of autoantibodies directed against human proteins. Alternatively, a custom protein array that includes autoantigens, such as those provided herein, for the detection of autoantibody biomarkers, can be used to assay for the presence of autoantibodies directed against human proteins.

The term "protein chip" is used in the present application synonymously with protein array or microarray.

Biomarkers

Protein biomarkers used in a protein array of the present invention may be the full protein or fragments of the full protein. Protein fragments are suitable for use as part of the protein array as long as the fragments contain the epitope recognized by the antibodies. The required epitope for a given full protein can be mapped using protein microarrays, and with ELISPOT or ELISA techniques. It is understood that the antigen biomarkers provided by the present invention are meant to encompass the full protein as well as fragments thereof comprising an epitope. Typically, suitable protein fragments comprise at least 5%, 6%, 7%, 8%, 9%; at least 10%, 11%, 12%, 13%, 14%, 15%, 16%, 17%, 18%, 19%; at least 20%, 25%, 30%, 35%, 45%; or at least 50%, 60%, 70%, 80%, 90% of the full length protein amino acid sequence. In one embodiment of the present invention, protein fragments contain at least 6 contiguous amino acids; at least 10 contiguous amino acids; at least 20 contiguous amino acids; at least 50 contiguous amino acids; at least 100 contiguous amino acids; or at least 200 contiguous amino acids of the full length protein.

"Biomarker" refers to a biochemical characteristic that can be used to detect, diagnose, prognose, direct treatment, or to measure the progress of a disease or condition, or the effects of treatment of a disease or condition. Biomarkers include, but are not limited to, the presence of a nucleic acid, protein, carbohydrate, or combination thereof, associated with the presence of a disease in an individual. Further examples of biomarkers include antibodies and cytokines.

As used herein, a "biomarker detection panel" or "biomarker panel" refers to a set of biomarkers that are provided together for detection, diagnosis, prognosis, staging, or monitoring of a disease or condition, based on detection values for the set (panel) of biomarkers.

One embodiment of the disclosure is a method of detecting one or more target antibodies in a test sample of an individual suspected of having an autoimmune disease, such as SLE, comprising: a) contacting the test sample from the individual with one or more target antigens of Table II or III, or a fragment thereof comprising an epitope; and b) detecting binding of the one or more target antigens, wherein the binding of the one or more target antigens detects the presence of the one or more target antibodies in the test sample.

In a further embodiment, the test sample is contacted with 1, 2, 3, 4, 5, 6, 7, 8, 9, 10, 11, 12, 13, 14, 15, 16, 17, 18, 19, 20, 21 or 22 of the antigens of Table III or fragments thereof comprising an epitope. In a further embodiment, the quantitative amount of antibodies that bind to each biomarker is determined.

In a further embodiment, at least 1, or any combination of 2, 3, 4, 5, 6, 7, 8, 9, 10, 11, 12, 13, 14, 15, 16, 17, 18, 19, 20, 21, 22 or more antigen biomarkers must be bound by an antibody from the test sample to indicate the presence of an autoimmune disease.

Another embodiment of the present disclosure is a method of diagnosing SLE in an individual comprising: a) contacting a test sample from the individual with one or more target antigens, each comprising an antigen of Table II or III, or a fragment thereof comprising an epitope; and b) detecting binding of the one or more target antigens to one or more antibodies in the test sample, wherein the presence of the one or more antibodies bound against the one or more target antigens is indicative of SLE.

In a further embodiment, the test sample is contacted with 1, 2, 3, 4, 5, 6, 7, 8, 9, 10, 11, 12, 13, 14, 15, 16, 17, 18, 19, 20, 21 or 22 of the antigens of Table II or III or fragments thereof comprising an epitope. In a further embodiment, the quantitative amount of antibodies that bind to each biomarker is determined.

In a further embodiment, at least 1, or any combination of 2, 3, 4, 5, 6, 7, 8, 9, 10, 11, 12, 13, 14, 15, 16, 17, 18, 19, 20, 21, 22 or more antigens of Table II or III or fragments thereof comprising an epitope are bound by an antibody from the test sample to indicate the presence of SLE.

Another embodiment of the disclosure is a mixture comprising one or more antigen(s) of Table II or III, or a fragment thereof comprising an epitope; and a test sample from an individual suspected of having SLE. The mixture optionally further comprises a control antibody against one or more of the target antigens. In a further embodiment, the mixture comprises 2, 3, 4, 5, 6, 7, 8, 9, 10, 11, 12, 13, 14, 15, 16, 17, 18, 19, 20, 21, or 22 of the antigens of Table II or III, or fragments thereof comprising an epitope. The test sample includes, but is not limited to, cells, tissues, or bodily fluids from an individual.

In other embodiments of the disclosure is provided a mixture comprising a test sample, a first affinity reagent, a second affinity reagent, a third affinity reagent and a purified antigen. In some embodiments, one or more of the affinity reagents is an antibody. In still other embodiments, the purified antigen is a transglutaminase.

In some embodiments of the disclosure is provided a mixture comprising a test sample, a first antibody that specifically binds RANTES, a second antibody that specifically binds RANTES, a third antibody that specifically binds human antibodies and a purified antigen, wherein the antigen is a transglutaminase. In other embodiments, the transglutaminase is guinea pig liver transglutaminase.

The disclosure identifies proteins that are selectively recognized by antibodies that represent an important pool of novel candidates for potential diagnostic markers or therapeutic targets.

Methods of Diagnosing

The present invention provides biomarkers for SLE that are antibodies present in the sera of subjects diagnosed with SLE. The biomarker antibodies in the present invention are the antibodies displaying increased reactivity in individuals with an autoimmune disease, most likely as a consequence of their increased abundance. These antibodies can be detected by contact with antigens.

The methods of the present invention are carried out on test samples derived from patients, including individuals suspected of having an autoimmune disease and those who have been diagnosed to have a disease. A "test sample" as used herein can be any type of sample, such as a sample of cells or tissue, or a sample of bodily fluid, preferably from an animal, most preferably a human. The sample can be a tissue sample, such as a swab or smear, or a pathology or biopsy sample of tissue, including tumor tissue. Samples can also be tissue extracts, for example from tissue biopsy or autopsy material. A sample can be a sample of bodily fluids, such as but not limited to blood, plasma, serum, sputum, semen, synovial fluid, cerebrospinal fluid, urine, lung aspirates, nipple aspirates, tears, or a lavage. Samples can also include, for example, cells or tissue extracts such as homogenates, cell lysates or solubilized tissue obtained from a patient. A preferred sample is a blood or serum sample.

By "blood" is meant to include whole blood, plasma, serum, or any derivative of blood. A blood sample may be, for example, serum.

A "patient" is an individual diagnosed with a disease or being tested for the presence of disease. A patient tested for a disease can have one or more indicators of a disease state, or can be screened for the presence of disease in the absence of any indicators of a disease state. As used herein an individual "suspected" of having a disease can have one or more indicators of a disease state or can be part of a population routinely screened for disease in the absence of any indicators of a disease state.

The individual from whom the test sample is taken can be any individual, healthy or suspected of having an autoimmune disease, more particularly, the individual is being screened for SLE.

By "an individual suspected of having an autoimmune disease," is meant an individual who has been diagnosed with SLE or who has at least one indicator of autoimmune disease, or who is at an increased risk of developing autoimmune disease due to age, environmental and/or nutritional factors, or genetic factors.

The phrase "diagnosis" as used herein refers to methods by which the skilled artisan can estimate and/or determine whether or not a patient is suffering from a given disease or condition. The skilled artisan often makes a diagnosis on the basis of one or more diagnostic indicators, that is, a marker, the presence, absence, or amount of which is indicative of the presence, severity, or absence of the condition, physical features (lumps or hard areas in or on tissue), or histological or biochemical analysis of biopsied or sampled tissue or cells, or a combination of these.

Similarly, a prognosis is often determined by examining one or more "prognostic indicators", the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability of having a disease or condition in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. For example, preferred prognostic markers can predict the onset of an autoimmune disease in a patient with one or more target antibodies of Table II or III, or a more advanced stage of an autoimmune disease in a patient diagnosed with the disease.

The term "correlating," as used herein in reference to the use of diagnostic and prognostic indicators, refers to comparing the presence or amount of the indicator in a patient to its presence or amount in persons known to suffer from, or known to be at risk of, a given condition; or in persons known to be free of a given condition. As discussed above, a marker level in a patient sample can be compared to a level known to be associated with autoimmune disease. The sample's marker level is said to have been correlated with a diagnosis; that is, the skilled artisan can use the marker level to determine whether the patient has an autoimmune disease, and respond accordingly. Alternatively, the sample's marker level can be compared to a marker level known to be associated with a good outcome (e.g., the absence of autoimmune disease, etc.). In preferred embodiments, a profile of marker levels are correlated to a global probability or a particular outcome using ROC curves.

The phrase "determining the prognosis" as used herein refers to methods by which the skilled artisan can predict the course or outcome of a condition in a patient. The term "prognosis" does not refer to the ability to predict the course or outcome of a condition with 100% accuracy, or even that a given course or outcome is more likely to occur than not. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. For example, in individuals not exhibiting the condition, the chance of a given outcome may be about 3%. In preferred embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to +/−1%.

The phrase "differentially present" refers to differences in the quantity of a biomolecule (such as an antibody) present in a sample taken from patients having an autoimmune disease as compared to a comparable sample taken from patients who do not have an autoimmune disease (for example, normal or healthy patients). A biomolecule is differentially present between the two samples if the amount of the polypeptide in one sample is significantly different from the amount of the polypeptide in the other sample. For example, a polypeptide is differentially present between the two samples if it is present in an amount (for example, concentration, mass, molar amount, etc.) at least about 150%, at least about 200%, at least about 500% or at least about 1000% greater or lesser than it is present in the other sample, or if it is detectable (gives a signal significantly greater than background or a negative control) in one sample and not detectable in the other. Any biomolecules that are differentially present in samples taken from autoimmune disease patients as compared to subjects who do not have an autoimmune disease can be used as biomarkers.

"Biomolecule" refers to an organic molecule of biological origin, for example, steroids, fatty acids, amino acids, nucleotides, sugars, peptides, polypeptides, antibodies, polynucleotides, complex carbohydrates or lipids.

The progression or remission of a disease can be monitored by contacting test samples from an individual taken at different times with the panel of antigens or cytokine specific capture antibodies. For example, a second test sample is taken from the patient and contacted with the antigen panel days or weeks after the first test sample. Alternatively, the second or subsequent test samples can be taken from the patient and tested against the panel of antigens at regular intervals, such as daily, weekly, monthly, quarterly, semi-annually, or annually. By testing the patient's test samples at different times, the presence of antibodies (and/or cytokines) and therefore the stage of the disease can be compared. A further embodiment of the invention is a method of monitoring one or more target antibodies in test samples from an individual diagnosed as having an autoimmune disease comprising: a) contacting a first test sample from the individual with a first set of one or more target antigens; b) detecting binding of the one or more target antigens, wherein the binding of the one or more target antigens detects the presence of the one or more target antibodies in the first test sample; c) contacting a second test sample from the individual with a second set of the one or more target antigens; d) detecting binding of the one or more target antigens, wherein the binding of the one or more target antigens detects the presence of the one or more target antibodies in the second test sample; and e) comparing the presence of the one or more antibodies bound against the one or more target antigens from the first test sample with the one or more antibodies bound against the one or more target antigens from the second test sample, wherein each of the one or more target antigens comprises an antigen of Table II or III, or fragments thereof comprising an epitope.

The progression of the disease is further monitored by quantitatively comparing the amounts of antibodies that bind to the antigens of Table II and Table III. Accordingly, another embodiment of the invention further comprises detecting the amount of the one or more antibodies against the one or more antigens in the first test sample and the second test sample; and comparing the amount of the one or more antibodies from the first test sample with the amount of the one or more antibodies from the second test sample.

"Sensitivity" is defined as the percent of diseased individuals (individuals with autoimmune disease) in which the biomarker of interest is detected (true positive number/total number of diseased.times.100). Nondiseased individuals diagnosed by the test as diseased are "false positives".

"Specificity" is defined as the percent of nondiseased individuals for which the biomarker of interest is not detected (true negative/total number without disease.times.100). Diseased individuals not detected by the assay are "false negatives." Subjects who are not diseased and who test negative in the assay, are termed "true negatives.

A "diagnostic amount" of a marker refers to an amount of a marker in a subject's sample that is consistent with a diagnosis of autoimmune disease. A diagnostic amount can be either in absolute amount (for example, X nanogram/ml) or a relative amount (for example, relative intensity of signals).

A "test amount" of a marker refers to an amount of a marker present in a sample being tested. A test amount can be either in absolute amount (for example, X nanogram/ml) or a relative amount (for example, relative intensity of signals).

A "control amount" of a marker can be any amount or a range of amount which is to be compared against a test amount of a marker. For example, a control amount of a marker can be the amount of a marker in an autoimmune disease patient, or a normal patient. A control amount can be either in absolute amount (for example, X nanogram/ml) or a relative amount (for example, relative intensity of signals).

Detection

In some embodiments, one or more affinity reagents are detectably labeled. In some embodiments the one or more affinity reagents are antibodies.

"Detect" refers to identifying the presence, absence or amount of the object to be detected.

"Label," "detectable label," or a "detectable moiety" refers to a composition detectable by spectroscopic, photochemical, biochemical, immunochemical, or chemical means. For example, useful labels include radiolabels such as $^{32}P$, $^{35}S$, or $^{125}I$; fluorescent dyes; chromophores, electron-dense reagents; enzymes that generate a detectable signal (for example, as commonly used in an ELISA); or spin labels. The label or detectable moiety has or generates a measurable signal, such as a radioactive, chromogenic, or fluorescent signal, that can be used to quantify the amount of bound detectable moiety in a sample.

Accordingly, in some embodiments the detectable label is a fluorescent label. In other embodiments, the detectable label is an enzymatic label.

The detectable moiety can be incorporated in or attached to a primer or probe either covalently, or through ionic, van der Waals or hydrogen bonds, for example, incorporation of radioactive nucleotides, or biotinylated nucleotides that are recognized by streptavidin. The label or detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavidin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P. D. Fahrlander and A. Klausner, Bio/Technology 6:1165 (1988)). Quantitation of the signal is achieved by, e.g., scintillation counting, densitometry, or flow cytometry.

Antibodies sometimes are derivatized with a functional molecule, such as a detectable label (e.g., dye, fluorophore, radioisotope, light scattering agent (e.g., silver, gold)) or binding agent (e.g., biotin, streptavidin), for example.

"Measure" in all of its grammatical forms, refers to detecting, quantifying or qualifying the amount (including molar amount), concentration or mass of a physical entity or chemical composition either in absolute terms in the case of quantifying, or in terms relative to a comparable physical entity or chemical composition.

The disclosure provides, in one aspect, a method of detecting one or more target antibodies in a test sample from an individual. The method includes: contacting a test sample from an individual with one or more target antigens of the invention, each comprising an antigen of Table II or III, or a fragment thereof that includes an epitope recognized by a target antibody; and detecting binding of one or more antibodies in the sample to one or more target antigens, thereby detecting the presence of the one or more target antibodies in the sample. The target antigen can be any of the target antigens provided in Table II or III, or a fragment thereof that includes an epitope. Furthermore, the target antigen can be a panel of target antigens that includes, for example, 2, 3, 4, 5, 6, 7, 8, 9, 10, 11, 12, 13, 14, 15, 16, 17, 18, 19, 20, or all target antigens of Table II or III. The method can be carried out using virtually any immunoassay method. Non-limiting examples of immunoassay methods are provided below.

Binding is typically detected using an immunoassay, which can be in various formats as described in detail below. Detection of binding in certain illustrative embodiments makes use of one or more solid supports to which the test antigen is immobilized on a substrate to which the sample from an individual, typically a human subject, is applied. After incubation of the sample with the immobilized antigen, or optionally, concurrently with the incubation of the sample, an antibody that is reactive against human antibodies (for example, an anti-human. IgG antibody that is from a species other than human, for example, goat, rabbit, pig, mouse, etc.) can be applied to the solid support with which the sample is incubated. The non-human antibody is directly or indirectly labeled. After removing nonspecifically bound antibody, signal from the label that is significantly above background level is indicative of binding of a human antibody from the sample to a test antigen on the solid support.

In the methods provided herein, the sample can be any sample of cells or tissue, or of bodily fluid. Since the antibodies being screened for circulate in the blood and are fairly stable in blood sample, in certain illustrative embodiments, the test sample is blood or a fraction thereof, such as, for example, serum. The sample can be unprocessed prior to contact with the test antigen, or can be a sample that has undergone one or more processing steps. For example, a blood sample can be processed to remove red blood cells and obtain serum.

The test sample can be contacted with a test antigen provided in solution phase, or the test antigen can be provided bound to a solid support. In preferred embodiments, the detection is performed by an immunoassay, as described in more detail below. Detection of binding of the target sample to a test antigen indicates the presence of an autoantibody that specifically binds the test antigen in the sample. Identifying an autoantibody present in a sample from an individual can be used to identify biomarkers of a disease or condition, or to diagnose a disease or condition.

The detection can be performed on any solid support, such as a bead, dish, plate, well, sheet, membrane, slide, chip, or array, such as a protein array, which can be a microarray, and can optionally be a high density microarray.

The detection method can provide a positive/negative binding result, or can give a value that can be a relative or absolute value for the level of the autoantibody biomarker in the sample. The result can provide a diagnosis, prognosis, or be used as an indicator for conducting further tests or evaluation that may or may not result in a diagnosis or prognosis.

The method includes detecting more than one autoantibody in a sample from an individual, in which one or more of the test antigens used to detect antibodies is a test antigen of Table II or III.

In some embodiments, the detection is performed on a protein array, which can be a microarray, and can optionally be a microarray that includes proteins at a concentration of at least $100/cm^2$ or $1000/cm^2$, or greater than $400/cm^2$.

The detection method can provide a positive/negative binding result, or can give a value that can be a relative or absolute value for the level of the autoantibody biomarker in the sample.

The method can be repeated over time, for example, to monitor a pre-disease state, to monitor progression of a disease, or to monitor a treatment regime. The results of a diagnostic test that determines the immune reactivity of a patient sample to a test antigen can be compared with the results of the same diagnostic test done at an earlier time. Significant differences in immune reactivity over time can contribute to a diagnosis or prognosis of autoimmune disease.

In certain embodiments, the biomarker detection panel has an ROC/AUC of 0.550 or greater, of 0.600 or greater, 0.650 or greater, 0.700 or greater, 0.750 or greater, 0.800 or greater, 0.850 or greater, or 0.900 or greater for distinguishing between a normal state and a disease state in a subject.

A target antigen present in a biomarker detection panel can be an entire mature form of a protein, such as a protein referred to as a target antigen (for example, a target antigen listed in Table II or III), or can be a precursor, processed form, unprocessed form, isoforms, variant, a fragment thereof that includes an epitope, or allelic variant thereof, providing that the modified, processed, or variant for of the protein has the ability to bind antigens present in samples from individuals.

In some embodiments, a biomarker detection panel used to detect autoimmune disease comprises one or more target antigens of Table 1. In some embodiments, a biomarker detection panel used to detect autoimmune disease comprises two or more target antigens of Table II or III. In some embodiments, a biomarker detection panel used to detect autoimmune disease comprises three or more target antigens of Table II or III. In some embodiments, a biomarker detection panel used to detect autoimmune disease comprises four or more target antigens of Table II or III. In some embodiments, the test sample is contacted with a biomarker detection panel comprising five or more target antigens of Table II or III. In some embodiments, the biomarker detection panel used in the methods of the disclosure includes six, seven, eight, nine, ten, eleven or twelve target antigens of Table II or III. In some embodiments, the biomarker detection panel used in the methods of the disclosure includes 12, 13, 14, 15 or more of the target antigens of Table II or III.

Immunoassays

"Immunoassay" is an assay in which an antibody specifically binds an antigen to provide for the detection and/or quantitation of the antibody or antigen. An immunoassay is characterized by the use of specific binding properties of a particular antibody to isolate, target, and/or quantify the antigen.

In some embodiments, a method is provided comprising contacting a test sample with three affinity reagents and a purified antigen, wherein the first two affinity reagents specifically bind RANTES and the third affinity reagent specifically binds a human antibody; detecting the presence or absence of binding of the three affinity reagents and thereby determining a binding level; comparing the binding level to a control binding level, wherein the control binding level is derived from a control sample comprising a test sample from a subject without systemic lupus erythematosus (SLE) wherein a difference between the binding level and the control binding level is a diagnostic indicator of SLE.

In other embodiments, a method is provided comprising contacting a test sample with three affinity reagents and a purified antigen, wherein the affinity reagents are antibodies. In some embodiments, the method further comprises providing a test sample. In other embodiments, the test sample is from a subject.

In still further embodiments, a method is provided wherein an immunosuppressive treatment or therapy is given.

In some embodiments, the method comprises an immunoassay. In still further embodiments, the immunoassay comprises at least on sandwich assay. In other embodiments, the immunoassay is protoplex immune response assay.

A "binding level" is the composite or the sum of detectable binding events for a particular affinity reagent/ligand interaction or for multiple affinity reagent/ligand interactions. A binding level can be qualitative or quantitive in nature.

Virtually any immunoassay technique known in the art can be used to detect antibodies that bind an antigen according to methods and kits of the present invention. Such immunoassay methods include, without limitation, radioimmunoassays, immunohistochemistry assays, competitive-binding assays, Western Blot analyses, ELISA assays, sandwich assays, two-dimensional gel electrophoresis (2D electrophoresis) and non-gel based approaches such as mass spectrometry or protein interaction profiling, all known to those of ordinary skill in the art. These methods may be carried out in an automated manner, as is known in the art. Such immunoassay methods may also be used to detect the binding of antibodies in a sample to a target antigen.

In one example of an ELISA method, the method includes incubating a sample with a target protein and incubating the reaction product formed with a binding partner, such as a secondary antibody, that binds to the reaction product by binding to an antibody from the sample that associated with the target protein to form the reaction product. In some cases these may comprise two separate steps, in others, the two steps may be simultaneous, or performed in the same incubation step. Examples of methods of detection of the binding of the target protein to an antibody, is the use of an anti-human IgG (or other) antibody or protein A. This detection antibody may be linked to, for example, a peroxidase, such as horseradish peroxidase.

Using protein arrays for immunoassays allows the simultaneous analysis of multiple proteins. For example, target antigens or antibodies that recognize biomarkers that may be present in a sample are immobilized on microarrays. Then, the biomarker antibodies or proteins, if present in the sample, are captured on the cognate spots on the array by incubation of the sample with the microarray under conditions favoring specific antigen-antibody interactions. The binding of protein or antibody in the sample can then be determined using secondary antibodies or other binding labels, proteins, or analytes. Comparison of proteins or antibodies found in two or more different samples can be performed using any means known in the art. For example, a first sample can be analyzed in one array and a second sample analyzed in a second array that is a replica of the first array.

The term "sandwich assay" refers to an immunoassay where the antigen is sandwiched between two binding reagents, which are typically antibodies. The first binding reagent/antibody is attached to a surface and the second binding reagent/antibody comprises a detectable moiety or label. Examples of detectable moieties include, for example and without limitation: fluorochromes, enzymes, epitopes for binding a second binding reagent (for example, when the second binding reagent/antibody is a mouse antibody, which is detected by a fluorescently-labeled anti-mouse antibody), for example an antigen or a member of a binding pair, such as biotin. The surface may be a planar surface, such as in the case of a typical grid-type array (for example, but without limitation, 96-well plates and planar microarrays), as described herein, or a non-planar surface, as with coated bead array technologies, where each "species" of bead is labeled with, for example, a fluorochrome (such as the Luminex technology described herein and in U.S. Pat. Nos. 6,599,331, 6,592,822 and 6,268,222), or quantum dot technology (for example, as described in U.S. Pat. No. 6,306,610).

A variety of different solid phase substrates can be used to detect a protein or antibody in a sample, or to quantitate or determine the concentration of a protein or antibody in a sample. The choice of substrate can be readily made by those of ordinary skill in the art, based on convenience, cost, skill, or other considerations. Useful substrates include without limitation: beads, bottles, surfaces, substrates, fibers, wires, framed structures, tubes, filaments, plates, sheets, and wells. These substrates can be made from: polystyrene, polypropylene, polycarbonate, glass, plastic, metal, alloy, cellulose, cellulose derivatives, nylon, coated surfaces, acrylamide or its derivatives and polymers thereof, agarose, or latex, or combinations thereof. This list is illustrative rather than exhaustive.

Other methods of protein detection and measurement described in the art can be used as well. For example, a single antibody can be coupled to beads or to a well in a microwell plate, and quantitated by immunoassay. In this assay format, a single protein can be detected in each assay. The assays can be repeated with antibodies to many analytes to arrive at essentially the same results as can be achieved using the methods of this invention. Bead assays can be multiplexed by employing a plurality of beads, each of which is uniquely labeled in some manner. For example each type of bead can contain a pre-selected amount of a fluorophore. Types of beads can be distinguished by determining the amount of fluorescence (and/or wavelength) emitted by a bead. Such fluorescently labeled beads are commercially available from Luminex Corporation (Austin, Tex.; see the worldwide web address of luminexcorp.com). The Luminex assay is very similar to a typical sandwich ELISA assay, but utilizes Luminex microspheres conjugated to antibodies or proteins (Vignali, J. Immunol. Methods 243:243-255 (2000)).

The methodology and steps of various antibody assays are known to those of ordinary skill in the art. Additional information may be found, for example, in Antibodies: A Laboratory Manual, Cold Spring Harbor Laboratory, Chap. 14 (1988); Bolton and Hunter, "Radioimmunoassay and Related Methods," in Handbook of Experimental Immunology (D. M. Weir, ed.), Blackwell Scientific Publications, 1996; and Current Protocols in Immunology, (John E. Coligan, et al., eds) (1993).

"Immune reactivity" as used herein means the presence or level of binding of an antibody or antibodies in a sample to one or more target antigens. A "pattern of immune reactivity" refers to the profile of binding of antibodies in a sample to a plurality of target antigens.

In certain embodiments, one or more diagnostic (or prognostic) biomarkers, such as one or more autoantibody biomarkers, are correlated to a condition or disease by the presence or absence of the biomarker(s). In other embodiments, threshold level(s) of a diagnostic or prognostic biomarker(s) can be established, and the level of the biomarker(s) in a sample can simply be compared to the threshold level(s).

As will be understood, for any particular biomarker, a distribution of biomarker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a biomarker changes with the disease) the test is considered to be abnormal and below which the test is considered to be normal. Receiver Operating Characteristic curves, or "ROC" curves, are typically generated by plotting the value of a variable versus its relative frequency in "normal" and "disease" populations. The area under the ROC curve is a measure of the probability that the perceived measurement will allow correct identification of a condition. ROC curves can also be generated using relative, or ranked, results. Methods of generating ROC curves and their use are well known in the art. See, e.g., Hanley et al., Radiology 143: 29-36 (1982).

One or more test antigens may have relatively low diagnostic or prognostic value when considered alone, but when used as part of a panel that includes other reagents for biomarker detection (such as but not limited to other test antigens), such test antigens can contribute to making a particular diagnosis or prognosis. In preferred embodiments, particular threshold values for one or more test antigens in a biomarker detection panel are not relied upon to determine if a profile of marker levels obtained from a subject are indicative of a particular diagnosis or prognosis. Rather, the present invention may utilize an evaluation of the entire marker profile of a biomarker detection panel, for example by plotting ROC curves for the sensitivity of a particular biomarker detection panel. In these methods, a profile of biomarker measurements from a sample of an individual is considered together to provide an overall probability (expressed either as a numeric score or as a percentage risk) that an individual has an autoimmune disease, for example. In such embodiments, an increase in a certain subset of biomarkers (such as a subset of biomarkers that includes one or more antibodies) may be sufficient to indicate a particular diagnosis (or prognosis) in one patient, while an increase in a different subset of biomarkers (such as a subset of biomarkers that includes one or more antibodies) may be sufficient to indicate the same or a different diagnosis (or prognosis) in another patient. Weighting factors may also be applied to one or more biomarkers being detected. As one example, when a biomarker is of particularly high utility in identifying a particular diagnosis or prognosis, it may be weighted so that at a given level it alone is sufficient to indicate a positive diagnosis. In another example, a weighting factor may provide that no given level of a particular marker is sufficient to signal a positive result, but only signals a result when another marker also contributes to the analysis.

In preferred embodiments, markers and/or marker panels are selected to exhibit at least 70% sensitivity, more preferably at least 80% sensitivity, even more preferably at least 85% sensitivity, still more preferably at least 90% sensitivity, and most preferably at least 95% sensitivity, combined with at least 70% specificity, more preferably at least 80% specificity, even more preferably at least 85% specificity, still more preferably at least 90% specificity, and most preferably at least 95% specificity. In particularly preferred embodiments, both the sensitivity and specificity are at least 75%, more preferably at least 80%, even more preferably at least 85%, still more preferably at least 90%, and most preferably at least 95%.

Using various subsets of the test antigens provided in Table II or III, the present disclosure provides test antibodies for detecting antibodies in a sample from an individual, antibodies for detecting autoimmune disease in an individual, and biomarker detection panels comprising combinations of the test antigens of Table 1 that can be used to detect and/or diagnose SLE with high sensitivity and specificity. Accordingly, methods, compositions, and kits are provided herein for the detection, diagnosis, staging, and monitoring of SLE in individuals.

Automated systems for performing immunoassays, such as those utilized in the methods herein, are widely known and used in medical diagnostics. For example, random-mode or batch analyzer immunoassay systems can be used, as are known in the art. These can utilize magnetic particles or non-magnetic particles or microparticles and can utilize a fluorescence or chemiluminescence readout, for example. As non-limiting examples, the automated system can be an automated microarray hybridization station, an automated liquid handling robot, the Beckman ACCESS paramagnetic-particle, an chemiluminescent immunoassay, the Bayer ACS:180 chemiluminescent immunoassay or the Abbott AxSYM microparticle enzyme immunoassay. Such automated systems can be designed to perform methods provided herein for an individual antigen or for multiple antigens without multiple user interventions.

Biomarker Detection Panels

The invention also provides biomarker detection panels for diagnosing, prognosing, monitoring, or staging SLE, in which the biomarker detection panels comprise two or more target antigens selected from Table II or III in which at least 50% of the proteins of the test panel are proteins of Table II or III. In some preferred embodiments, the proteins of the biomarker detection panel are provided on one or more solid supports, in which at least 50% of the proteins on the one or more solid supports to which the proteins of the panel are bound are of Table II or III. Proteins of a biomarker detection panel can be provided bound to a solid support in the form of a bead, matrix, dish, well, plate, slide, sheet, membrane, filter, fiber, chip, or array. In some preferred embodiments, the proteins of the biomarker detection panel are provided on a protein array in which 50% or more of the proteins on the array are target antigens of the biomarker detection panel.

The set of biomarkers in a biomarker detection panel are associated, either electronically, or preferably physically. For example, each biomarker of a biomarker detection panel can be provided in isolated form, in separate tubes that are sold and/or shipped together, for example as part of a kit. In certain embodiments, isolated biomarkers are formed into a detection panel by attaching them to the same solid support. The biomarkers of a biomarker panel can also be mixed together in the same solution.

The invention also provides biomarker detection panels for diagnosing, prognosing, monitoring, or staging autoimmune disease, in which the biomarker detection panels comprise 2, 3, 4, 5, 6, 7, 8, 9, 10, or more target antigens selected from Table II or III.

In some embodiments, the biomarker detection panel used in the methods of the disclosure includes 6, 7, 8, 9, 10, 11, or 12, 13, 14, 15, or more target antigens of Table II or III In some embodiments, the test sample is contacted with a biomarker detection panel comprising 6, 7, 8, 9, 10, 11, or 12, 13, 14, 15, or more target antigens of Table II or III.

Methods for Synthesizing Protein Antigens

The methods, kits, and systems provided herein include autoantigens, which typically are protein antigens. To obtain protein antigens to be used in the methods provided herein, known methods can be used for making and isolating viral, prokaryotic or eukaryotic proteins in a readily scalable format, amenable to high-throughput analysis. For example, methods include synthesizing and purifying proteins in an array format compatible with automation technologies. Therefore, in one embodiment, protein microarrays for the invention a method for making and isolating eukaryotic proteins comprising the steps of growing a eukaryotic cell transformed with a vector having a heterologous sequence operatively linked to a regulatory sequence, contacting the regulatory sequence with an inducer that enhances expression of a protein encoded by the heterologous sequence, lysing the cell, contacting the protein with a binding agent such that a complex between the protein and binding agent is formed, isolating the complex from cellular debris, and isolating the protein from the complex, wherein each step is conducted in a 96-well format.

In a particular embodiment, eukaryotic proteins are made and purified in a 96-array format (i.e., each site on the solid support where processing occurs is one of 96 sites), e.g., in a 96-well microtiter plate. In another embodiment, the solid support does not bind proteins (e.g., a non-protein-binding microtiter plate).

In certain embodiments, proteins are synthesized by in vitro translation according to methods commonly known in the art. For example, proteins can be expressed using a wheat germ, rabbit reticulocyte, or bacterial extract, such as the Expressway.

Any expression construct having an inducible promoter to drive protein synthesis can be used in accordance with the methods of the invention. The expression construct may be, for example, tailored to the cell type to be used for transformation. Compatibility between expression constructs and host cells are known in the art, and use of variants thereof are also encompassed by the invention.

In a particular embodiment, the fusion proteins have GST tags and are affinity purified by contacting the proteins with glutathione beads. In further embodiment, the glutathione beads, with fusion proteins attached, can be washed in a 96-well box without using a filter plate to ease handling of the samples and prevent cross contamination of the samples.

In addition, fusion proteins can be eluted from the binding compound (e.g., glutathione bead) with elution buffer to provide a desired protein concentration. In a specific embodiment, fusion proteins are eluted from the glutathione beads with 30 µl of elution buffer to provide a desired protein concentration For purified proteins that will eventually be spotted onto microscope slides, the glutathione beads are separated from the purified proteins. In one example, all of the glutathione beads are removed to avoid blocking of the microarrays pins used to spot the purified proteins onto a solid support. In one embodiment, the glutathione beads are separated from the purified proteins using a filter plate, for example, comprising a non-protein-binding solid support. Filtration of the eluate containing the purified proteins should result in greater than 90% recovery of the proteins.

The elution buffer may, for example, comprise a liquid of high viscosity such as, for example, 15% to 50% glycerol, for example, about 25% glycerol. The glycerol solution stabilizes the proteins in solution, and prevents dehydration of the protein solution during the printing step using a microarrayer.

Purified proteins may, for example, be stored in a medium that stabilizes the proteins and prevents desiccation of the sample. For example, purified proteins can be stored in a liquid of high viscosity such as, for example, 15% to 50% glycerol, for example, in about 25% glycerol. In one example, samples may be aliquoted containing the purified proteins, so as to avoid loss of protein activity caused by freeze/thaw cycles.

The skilled artisan can appreciate that the purification protocol can be adjusted to control the level of protein purity desired. In some instances, isolation of molecules that associate with the protein of interest is desired. For example, dimers, trimers, or higher order homotypic or heterotypic complexes comprising an overproduced protein of interest can be isolated using the purification methods provided herein, or modifications thereof. Furthermore, associated molecules can be individually isolated and identified using methods known in the art (e.g., mass spectroscopy).

The protein antigens once produced can be used in the biomarker panels, methods and kits provided herein as part of a "positionally addressable" array. The array includes a plurality of target antigens, with each target antigen being at a different position on a solid support. The array can include, for example 1, 2, 3, 4, 5, 8, 9, 10, 11, 12, 13, 14, 15, 16, 17, 18, 19, 20, 21, 22, 23, 24, 25, 26, 27, 28, 29, 30, 40, 50, 100, 200, 300, 400, or 500 different proteins. The array can include 1, 2, 3, 4, 5, 10, 11, 12, 13, 14, 15, 16, 17, 18, 19, 20, or more target antigens of Table II or III. In one aspect, the majority of proteins on an array include proteins identified as autoantigens that can have diagnostic value for a particular disease or medical condition when provided together autoantigen biomarker detection panel.

In one aspect, the protein array is a bead-based array. In another aspect, the protein array is a planar array. Methods for making protein arrays, such as by contact printing, are well known. In some embodiments, the detection is performed on a protein array, which can be a microarray, and can optionally be a microarray that includes proteins at a concentration of at least $100/cm^2$ or $1000/cm^2$, or greater than $400/cm^2$.

Kits

In certain embodiments of the invention, kits are provided. Thus, in some embodiments, a kit is provided that comprises 1, 2, 3, 4, 5, 6, 7, 8, 9, 10, 11, 12, 13, 14, or 15 or more of the test antigen proteins provided in Table II or III. A kit of the invention can include any of the biomarker detection panels disclosed herein, including, but not limited to, a biomarker panel comprising two or more test antigens of Table II or III.

In one embodiment, a kit for diagnosing SLE comprises one or more, two or more, ten or more, or all of the antigens of Table II or III or a fragment thereof comprising an epitope; and means for detecting if one or more molecules in a test sample binds to one or more of the antigens. In a further embodiment, the kit further comprises a control antibody against one or more of the antigens.

In a further embodiment, the kit comprises one or more, two or more, ten or more, or all of the antigens selected from the group comprising of Table II or III or fragments thereof comprising an epitope.

The kit can include one or more positive controls, one or more negative controls, and/or one or more normalization controls.

The proteins of the kit may, for example, be immobilized on a solid support or surface. The proteins may, for example, be immobilized in an array. The protein microarray may use bead technology, such as the Luminex technology (Luminex Corp., Austin, Tex.). The test protein array may or may not be a high-density protein microarray that includes at least 100 proteins/cm.sup.2. The kit can provide a biomarker detection panel of proteins as described herein immobilized on an array. At least 50%, at least 55%, at least 60%, at least 65%, at least 70%, at least 75%, at least 80%, at least 85%, at least 90%, or at least 95% of the proteins immobilized on the array can be proteins of the biomarker test pane. The array can include immobilized on the array one or more positive control proteins, one or more negative controls, and/or one or more normalization controls.

A kit may further comprise a reporter reagent to detect binding of human antibody to the proteins, such as, for example, an antibody that binds to human antibody, linked to a detectable label. A kit may further comprise reagents useful for various immune reactivity assays, such as ELISA, or other immunoassay techniques known to those of skill in the art. The assays in which the kit reagents can be used may be competitive assays, sandwich assays, and the label may be selected from the group of well-known labels used for radioimmunoassay, fluorescent or chemiluminescence immunoassay.

A kit can include reagents described herein in any combination. For example, in one aspect, the kit includes a biomarker detection panel as provided herein immobilized on a solid support and anti-human antibodies for detection in solution. The detection antibodies can comprise labels.

The kit can also include a program in computer readable form to analyze results of methods performed using the kits to practice the methods provided herein.

The kits of the present invention may also comprise one or more of the components in any number of separate containers, packets, tubes, vials, microtiter plates and the like, or the components may be combined in various combinations in such containers.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Example I: Detection of Autoantibodies in the Serum of SLE Patients Using a Protein Microarray A study was conducted with 33 SLE patient serum? samples and 41 negative serum ?control samples to identify novel autoantibody responses. These samples were screened on the Invitrogen, PROTOARRAY® Human Protein Microarray v5.0 following the manufacturer's protocol. Briefly, microarray slides were initially treated with blocking buffer (Invitrogen PrtotoArray® Kit) at 4° C. for 1 h with gentle agitation. After blocking, arrays were removed and probed for 2 h at 4° C. with a 1:10 dilution of each sample diluted in freshly prepared PBST buffer (1×PBS, 01.% Tween-20 and 1% BSA). Afterwards, the arrays were washed 5 times with PBST buffer. An AlexaFluor 647-conjugated goat anti-human IgG antibody diluted to a final concentration of 1 ug/ml was then applied to each array and allowed to incubate with gentle shaking at 4° C. for 90 min. After this incubation, excess antibody was removed by washing with PBST buffer and the arrays were then scanned using an Axon GenePix 400B fluorescent microarray scanner. The results were then analyzed using the Prospector Imager and Analyzer (Invitrogen). A negative control assay was run in parallel with the samples as described below. Since each protein occurs twice on the array, the mean values of duplicates from the array are used for data analysis.

In the negative control assay, a protein microarray was treated in identical manner to the experimental assay, except that is was incubated in a buffer containing no serum prior to incubation with the AlexaFluor® 647-conjugated goat anti-human IgG antibody. Each ProtoArray microarray contains control proteins (AlexaFluor®-conjugated antibody, human IgG, etc), which are used to provide reference points for data acquisition and analysis. The AlexaFluor®-conjugated antibody allows proper alignment of the spot-finding software for data acquisition. Each subarray contains a gradient of human IgG, which serves as a control for proper performance of the detection reagent. In addition, anti-human IgG antibody is spotted as a gradient in every subarray. The antibody binds to IgG present in the saliva sample and serves as a positive control for proper assay performance.

Positive immune responses in the disease specific samples were identified using the M-statistics function in PROTOARRAY® Prospector software. The software performs all aspects of the analysis, including background correction, normalization, and statistical calculations of significance.

This initial screening identified autoantibodies to 57 candidate biomarkers (see Table 1) which were elevated in the SLE samples as compared to healthy control samples (see Table 1).

PROTOPLEX™ immune response assay. The prevalence and statistical significance (M statistics) of these autoimmune responses markers with SLE samples and control samples was calculated.

TABLE I

57 Candidate SLE BIOMARKERS

| | | |
|---|---|---|
| B01R04C07~BC005332.1 | B33R02C19~NM_006223.1 | B14R13C09~NM_005371.2 |
| B01R14C07~NM_032359.1 | B33R12C07~BC026104.2 | B15R06C17~BC063275.1 |
| B01R15C17~PV4215 | B34R04C13~BC038953.1 | B15R09C05~NM_031303.1 |
| B01R16C07~NM_005801.2 | B34R07C09~NM_017629.2 | B17R04C03~BC004967.1 |
| B01R17C01~NM_012280.1 | B34R09C01~NM_018439.1 | B21R05C01~NM_004645.1 |
| B01R20C07~BC005914.1 | B34R19C07~BC032749.1 | B21R19C09~NM_001821.2 |
| B02R20C13~NM_006521.3 | B36R16C11~BC024209.1 | B22R08C17~NM_004728.2 |
| B05R05C01~NM_002391.1 | B38R02C13~BC057237.1 | B24R18C21~NM_005526.1 |
| B05R12C01~NM_145212.1 | B38R02C17~BC035973.1 | B25R18C19~BC066958.1 |
| B05R12C21~BC002940.1 | B38R17C15~BC017305.1 | B26R15C17~PV3817 |
| B06R08C17~BC017258.2 | B40R02C13~BC023569.1 | B27R08C09~NM_001008572.1 |
| B09R02C21~BC041009.2 | B40R14C05~NM_033256.1 | B28R08C15~NM_004058.2 |
| B09R12C07~BC016842.1 | B41R17C15~BC001494.1 | B28R12C17~NM_198081.1 |
| B09R15C13~Ro/SS~A Antigen | B43R15C11~NM_000854.2 | B29R04C01~BC015416.1 |
| | B44R06C09~BC026039.1 | B29R16C15~NM_002904.4 |
| B09R17C03~BC012566.1 | B44R13C17~NM_152576.1 | B32R02C17~NM_007194.2 |
| B10R04C15~NM_004526.2 | B46R15C13~RNP_COMPLEX | B32R17C19~NM_001003712.1 |
| B10R08C07~NM_052969.1 | B46R15C21~PV3822 | |
| B11R05C11~BC007957.1 | B47R15C05~NM_022777.1 | |
| B11R17C03~BC021983.1 | B47R20C05~BC043391.1 | |
| B13R09C05~XM_378988.2 | | |

Example II: Validation of Autoantibody Biomarkers

ProtoPlex™ Immune Response Assay was used as an orthogonal platform for validation of the antibodies to the antigens found in Table II and III identified in SLE samples (see FIG. 1). GST fusion proteins are expressed in insect cells and captured on SEROMAP™ microspheres via an anti-GST antibody. Protein-coupled beads are multiplexed and aliquoted into 96 well plates and incubated with patient samples. Antibodies present in the samples bind to antigens, and this binding is detected using an anti-human IgG coupled secondary antibody labeled with RPE, followed by bead interrogation in a LUMINEX® instrument.

Figure 2:
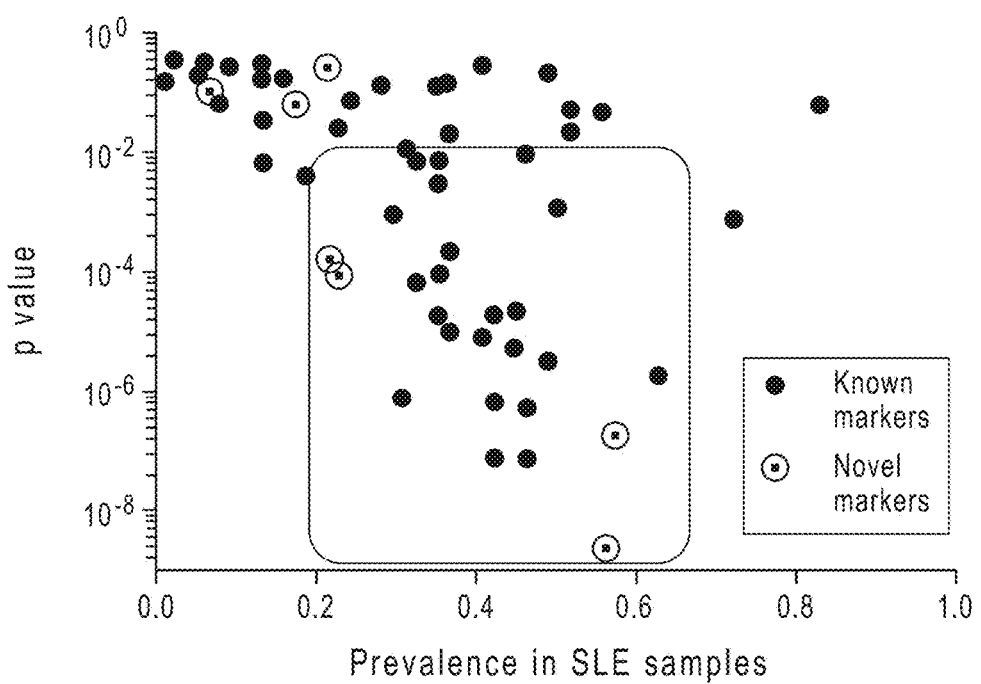
FIG. 2 is a graph of the immune response p-values and prevalence as calculated for each antigen (dots=known SLE markers; dots with concentric circle=novel markers). High reliability responses that displayed prevalence greater than 20% are within the box.
Figure 4A:
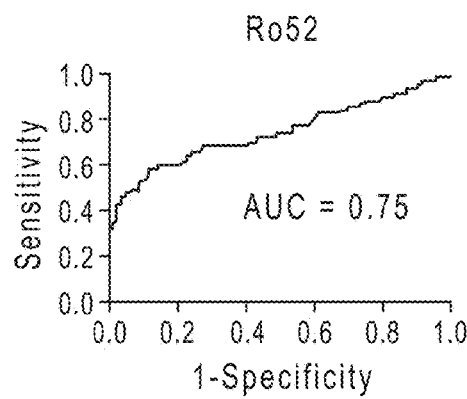
FIG. 4A-D is a series of graphs of sensitivity (y-axis) and specificity (x-axis) SLE biomarkers Ro52 (A), RNP complex (B), EIF2C1 (C), and HMGN1 (D). Area under the curve (AUC) was calculated for each marker.
Figure 4B:
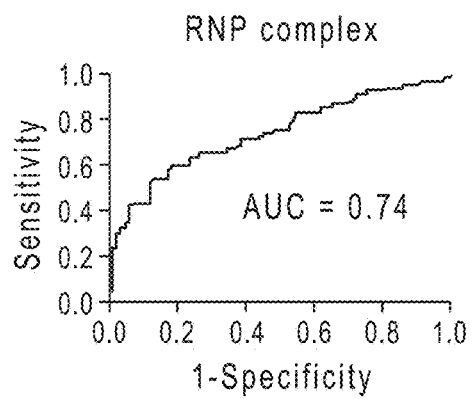
Figure 4C:
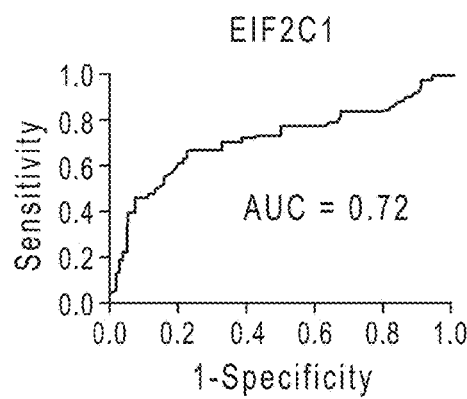
Figure 4D:
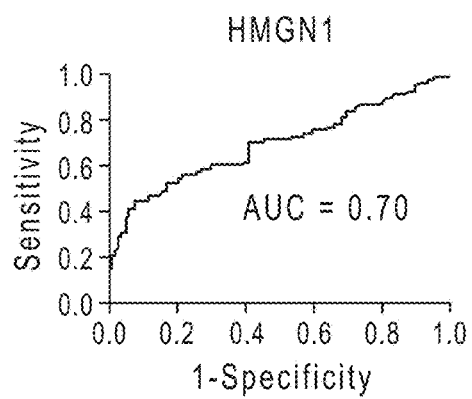
Figures 5A, 5B, 5C:
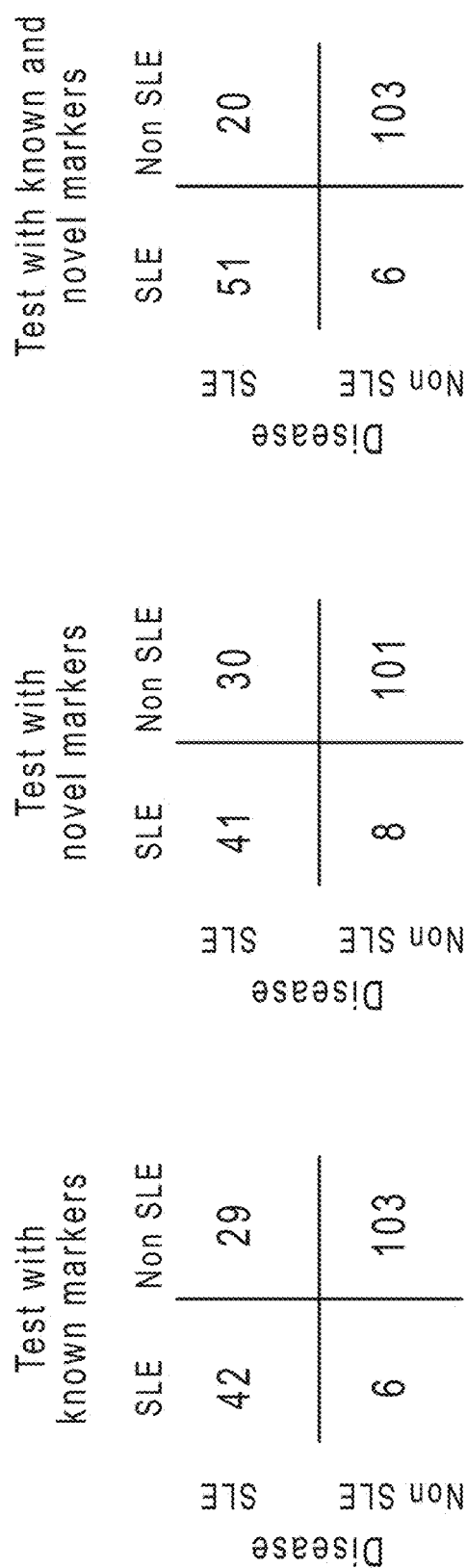
FIG. 5A-C is a series of grids showing the sensitivity and specificity of new (A), established (B), and combined SLE markers (C).
Figure 6A:
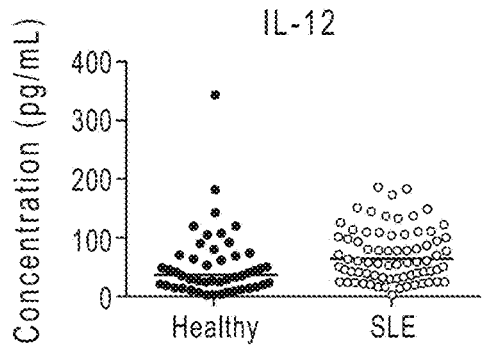
FIG. 6A-E displays the distribution of serum cytokine levels: (A) IL-12, (B) IL2R, (C) IL-13, (D) Eotaxin, and (E) Rantes, among 177 human serum samples tested, healthy controls and individuals diagnosed with SLE.
Figure 6B:
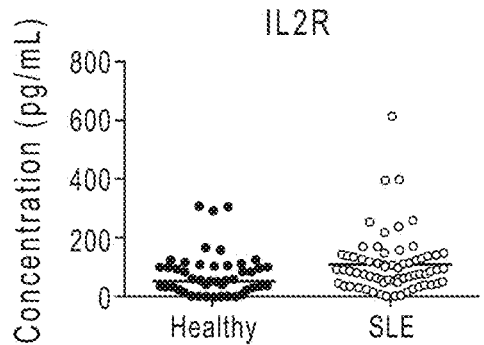
Figure 6C:
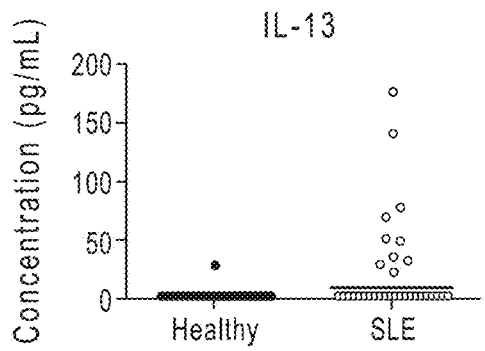
Figure 6D:
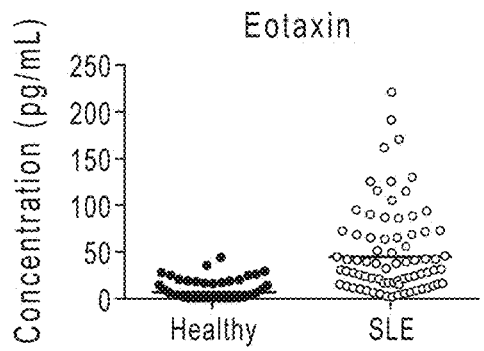
Figure 6E:
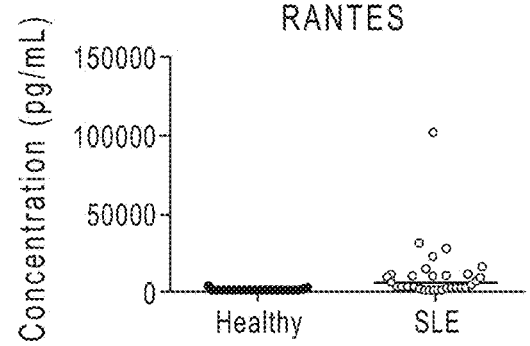
Figure 7A:
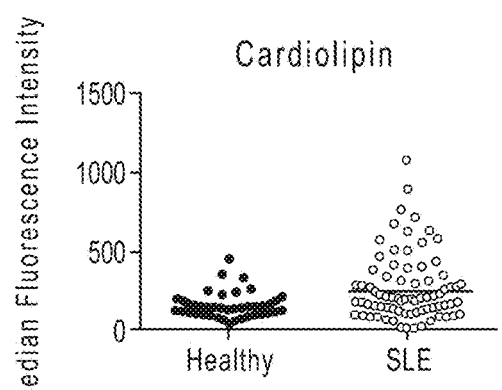
FIG. 7A-7J displays the distribution of serum antibody levels against particular proteins among 177 human serum samples from healthy controls and individuals diagnosed with SLE. Proteins are FIG. 7(A) cardiolipin, FIG. 7(B) centromere Protein B (CENP B), FIG. 7(C) Jo-1, FIG. 7(D) transglutaminase, FIG. 7(E) Mi-2b, FIG. 7(F) myeloperoxidase, FIG. 7(G) Ro/SS-A, FIG. 7(H) smith-antigen (Sm), FIG. 7(I) thyroglobulin, and FIG. 7(J) thyroid peroxidase.
Figure 7B:
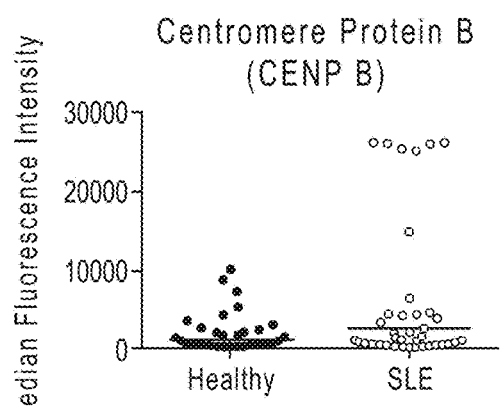
Figure 7C:
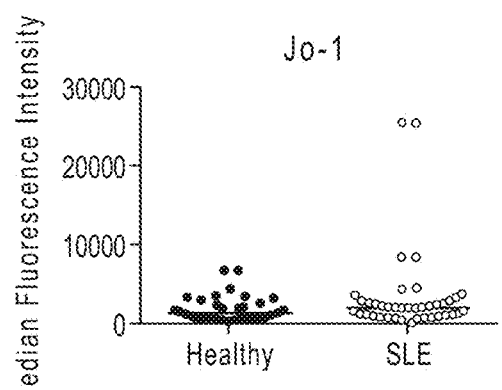
Figure 7D:
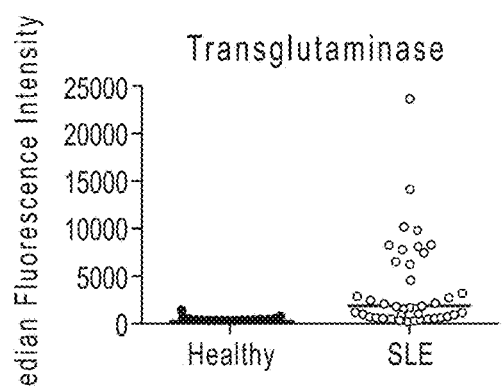
Figure 7E:
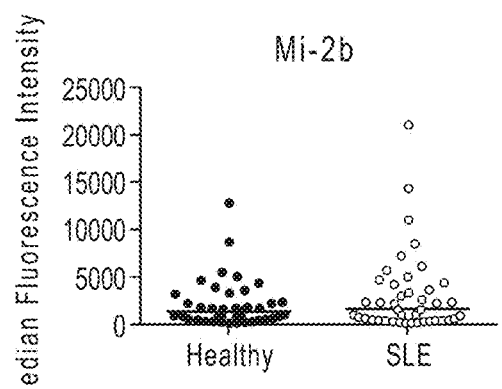
Figure 7F:
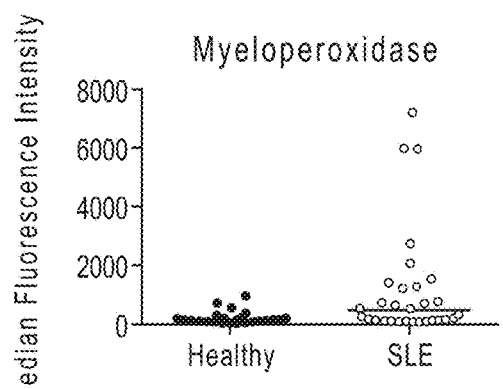
Figure 7G:
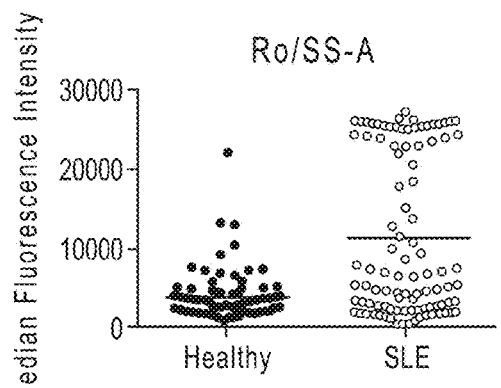
Figure 7H:
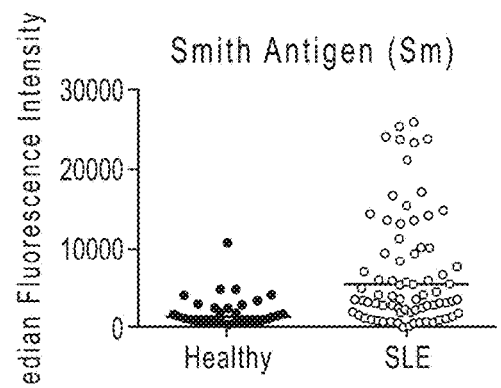
Figure 7I:
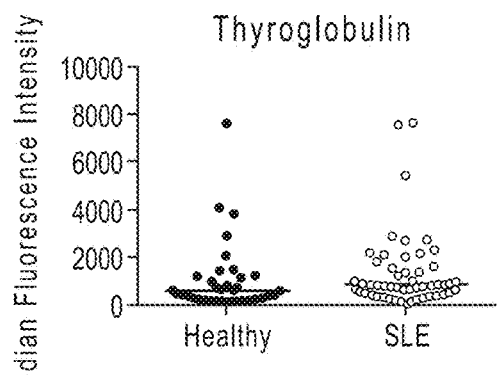
Figure 7J:
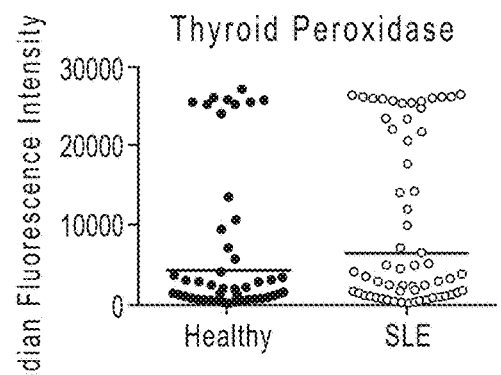

Example III: Validation of Candidate Biomarkers in a New Cohort of Patient Samples To validate the candidate biomarkers discovered in the PROTOARRAY® assay of Example I, a new cohort of 108 total age-matched samples; 71 SLE patient samples, 50 control subject samples, and 59 non-related disease (Crohn's disease, rheumatoid arthritis, and multiple sclerosis) samples were profiled using the PROTOPLEX™ Immune Response Assay for their immune responses to these 47 candidate biomarkers and 7 SLE autoantigens (SCL-70, CENP-B, La/SS-B, RNP complex, Ro/SS-A, Jo-1) established previously in Example I. Four of the established markers and 15 of the candidate biomarkers had statistically significant p-values and prevalence greater than 20% in the SLE population (FIGS. 2, 3, and Table II). Further, 12 of the 15 novel markers demonstrated comparable performance to established markers based on the area under the curve (AUC) for the markers (FIG. 4). Sensitivity and specificity of new, established, and combined new and established SLE markers is shown in FIG. 5. A combined panel of known and novel SLE biomarkers are shown in Table III.

The novel SLE auto-antigens in shown in FIG. 3 were characterized for the corresponding immune responses using

TABLE II

15 Novel SLE Biomarkers

| | |
|---|---|
| DDX54 | C1orf77 |
| NPM1 | EIF2C1 |
| HMGN1 | RPS19 |
| RDBP | SNRP70 |
| METTL1 | PIN4 |
| EIF2C4 | C3orf26 |
| MRPS6 | PPP1R14A |
| C1orf83 | |

TABLE III

22 SLE Biomarker Panel

| | |
|---|---|
| DDX54 | C1orf77 |
| NPM1 | EIF2C1 |
| HMGN1 | RPS19 |
| RDBP | SNRP70 |
| METTL1 | PIN4 |
| EIF2C4 | C3orf26 |
| MRPS6 | PPP1R14A |
| C1orf83 | SCL-70 |
| CENP-B | transglutaminase |
| La/SS-B | RNP complex |
| Ro/SS-A, | Jo-1 |

Example IV

To explore novel methods to improve the predictive power of SLE biomarker identification (increased percent correctly classified instances, and decreased number of markers in a panel), we examined the impact of performing combined cytokine and autoantibody immune profiling. The Novex 30-plex human cytokine magnetic panel (LHC6003M, Table 4) and the Novex 19-plex autoantigen panel (Table 5) were used utilized in the serum profiling of 92 SLE, and 85 healthy control samples. Each kit was run according to manufacturer suggested guidelines. Feature selection was based upon the Weka data mining tool (Mark Hall, Eibe Frank, Geoffrey Holmes, Bernhard Pfahringer, Peter Reutemann, Ian H. Witten [2009]; *The WEKA Data Mining Software: An Update; SIGKDD Explorations,* Volume 11, Issue 1.) was used for the feature selection analysis. The generated .csv file of signal intensity, with serum sample classification (healthy or SLE) on each row and protein name on each column was used as the input into the software. Each antigen or cytokine was treated as a single biomarker selected by M-Stat algorithm (see description about M-Stat) WrapperSubsetEval method, an evaluator method that evaluates attribute sets by a learning scheme (Ron Kohavi, George H. John [1997]. *Wrappers for feature subset selection. Artificial Intelligence.* 97 [1-2]:273-324) was selected, with logistic regression selected as the algorithm for learning. A 10-fold cross validation was used to reduce over fitting and estimate the accuracy of the learning scheme for a set of attributes. The feature set, i.e. the subset of protein markers are reported by the software, with the prediction error rate in a confusion matrix.

TABLE IV

Novex 30-plex human cytokine magnetic panel

| | |
|---|---|
| EGF | IFN-gamma |
| IL-2 | IL-10 |
| IL-15 | RANTES |
| HGF | G-CSF |
| IL-7 | IL-5 |
| MIP-1 alpha | MCP-1 |
| Eotaxin | IL-RA |
| IL-2R | IL-12 |
| IL-17 | TNF-alpha |
| IFN-alpha | GM-CSF |
| IL-8 | IL-6 |
| MIP-1 beta | MIG |
| FGF-basic | IL-1 beta |
| IL-4 | IL-13 |
| IP-10 | VEGFA |

TABLE V

Novex 19-plex human autoantigen panel

| | |
|---|---|
| Cardiolipin | Ro/SS-A antigen |
| Centromere protein B | Scl-34 |
| H2a(F2A2) & H4(F2A1) | Scl-70 antigen |
| Histone-type IIA | Smith antigen |
| Jo-1 | Thyroglobulin |
| La/SS-B antigen | Thyroid peroxidase |
| Mi-2b | Transglutaminase |
| Myeloperoxidase | U1-snRNP 68 |
| Proteinase-3 | RNP complex |
| Pyruvate Dehydrogenase | |

Performing serum profiling on all 85 healthy and 92 SLE serum samples with the Novex 30-plex human cytokine magnetic panel resulted in identification of a 5-plex cytokine panel that is 98% predictive of SLE (FIGS. 6 and 8a). Testing these same 177 serum samples utilizing the Novex 19-plex human autoantigen panel produced data indicating a 9-plex autoantibody sub-set that is 80% predictive of disease (FIGS. 7 and 8b). Examining all data (30-plex cytokine and 19-plex autoantibody) from the 177 serum sample set, identified a statistically powerful 2-plex (cytokine and autoantibody) that is 98% predictive of SLE (FIG. 8c).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention. The term "or" is not meant to be exclusive to one or the terms it designates. For example, as it is used in a phrase of the structure "A or B" may denote A alone, B alone, or both A and B. Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

We claim:

1. A method of determining a biomarker profile in a sample from a subject, comprising:
   contacting a sample comprising serum from a subject with three antibodies, wherein the first two antibodies specifically bind RANTES and the third antibody specifically binds a human autoantibody, wherein the human autoantibody specifically binds transglutaminase, and contacting the sample with a purified antigen comprising transglutaminase; and
   detecting a presence or absence of binding, and optionally a quantity of binding, of RANTES with the first two antibodies, and detecting a presence or absence of binding, and optionally a quantity of binding, of the human autoantibody with the third antibody and the purified antigen, and determining a binding profile therefrom.

2. The method of claim 1, further comprising contacting the sample with a biomarker selected from the group consisting of cardiolipin, CENP B, Jo-1, Mi-2b, myeloperoxidase, Ro/SS-A, Smith Antigen, thyroglobulin, and thyroid peroxidase, and an additional antibody which specifically binds a second autoantibody that specifically binds the biomarker, detecting a presence or absence of binding, and optionally a quantity of binding, of the second autoantibody with the biomarker and the additional antibody, and including the detected presence, absence or quantity in the binding profile determination.

3. The method of claim 1, further comprising contacting the sample with an additional antibody that specifically binds a biomarker selected from the group consisting of IL13, IL12, eotaxin, and IL 2R, detecting a presence or absence of binding of the additional antibody with the biomarker, and optionally a quantity of binding of the additional antibody with the biomarker, and including the detected presence, absence or quantity in the binding profile determination.

4. The method of claim 1, wherein the two antibodies that specifically bind RANTES are monoclonal antibodies and recognize different epitopes, and wherein one of the two antibodies that specifically bind RANTES and the antibody that specifically binds the human autoantibody are labeled.

5. The method of claim 4, wherein the labeled antibodies are differentially labeled.

6. The method of claim 5, wherein the labels are fluorescent.

7. The method of claim 4, wherein one of the two antibodies that specifically bind RANTES is not labeled and is immobilized on a solid surface.

8. The method of claim 7, wherein the solid surface is a microarray.

9. The method of claim 1, further comprising contacting the sample with additional antibodies that respectively specifically bind biomarkers IL13, IL12, eotaxin, and IL 2R, detecting a presence or absence of binding of the respective additional antibodies with the biomarkers, and optionally quantities of binding of the respective additional antibodies with the biomarkers, and including each respective detected presence, absence or quantity in the binding profile determination.

10. The method of claim 1, wherein the purified antigen comprising transglutaminase is guinea pig liver transglutaminase.

11. The method of claim 1, wherein the purified antigen is immobilized on a solid surface.

12. The method of claim 11, wherein the solid surface is a microarray.

13. The method of claim 1, wherein one of the two antibodies that specifically bind RANTES is not labelled and is immobilized on a solid surface, and wherein the purified antigen is immobilized on the solid surface.

14. The method of claim 13, wherein the solid surface is a microarray.

15. A method of determining a biomarker profile in a sample from a subject, comprising:
 providing a kit comprising three antibodies, wherein first and second antibodies specifically bind RANTES and a third antibody specifically binds a human autoantibody, wherein the human autoantibody specifically binds transglutaminase,
 contacting a sample comprising serum from a subject with the three antibodies, and contacting the sample with a purified antigen comprising transglutaminase; and
 detecting a presence or absence of binding, and optionally a quantity of binding, of RANTES with the first and second antibodies, and detecting a presence or absence of binding, and optionally a quantity of binding, of the human autoantibody with the third antibody and the purified antigen, and determining a binding profile therefrom.

16. The method of claim 15, wherein the kit comprises one of the two antibodies that specifically bind RANTES immobilized on a solid surface and the purified antigen immobilized on the solid surface.

17. The method of claim 16, wherein the solid surface is a microarray.

18. The method of claim 16, wherein one of the two antibodies that specifically bind RANTES is not immobilized on the solid support and has a first detectable label bound thereto, and wherein a second detectable label is bound to the third antibody.

19. A method of determining biomarkers in a sample from a subject, comprising:
 providing a kit comprising three antibodies and a purified antigen, wherein first and second antibodies specifically bind RANTES and a third antibody specifically binds a human autoantibody, wherein the human autoantibody specifically binds transglutaminase and the purified antigen comprises transglutaminase, wherein one of the two antibodies that specifically bind RANTES is immobilized on a solid surface and the purified antigen is immobilized on the solid surface, and wherein the other of the two antibodies that specifically bind RANTES is not immobilized on the solid support and has a first detectable label bound thereto, and wherein a second detectable label is bound to the third antibody;
 contacting a sample comprising serum from a subject with the three antibodies and the purified antigen comprising transglutaminase; and
 detecting a presence or absence of binding, and optionally a quantity of binding, of RANTES with the first and second antibodies, and detecting a presence or absence of binding, and optionally a quantity of binding, of the human autoantibody with the third antibody and the purified antigen.

* * * * *